US008778298B2

(12) United States Patent
Takashima et al.

(10) Patent No.: US 8,778,298 B2
(45) Date of Patent: Jul. 15, 2014

(54) ISOTOPE LABELED 2-ARYLPROPIONIC ACID COMPOUNDS AND PROCESS FOR PRODUCTION OF SAME, AND MOLECULAR PROBE FOR POSITRON EMISSION TOMOGRAPHY AND METHOD FOR IMAGING OF CYCLOOXYGENASE AND THE LIKE USING SAME

(75) Inventors: Misato Takashima, Kobe (JP); Miho Shukuri, Kobe (JP); Miki Goto, Kobe (JP); Hisashi Doi, Kobe (JP); Hirotaka Onoe, Kobe (JP); Masaaki Suzuki, Kobe (JP); Yasuyoshi Watanabe, Kobe (JP)

(73) Assignee: Riken, Saitama (JP)

( * ) Notice: Subject to any disclaimer, the term of this patent is extended or adjusted under 35 U.S.C. 154(b) by 131 days.

(21) Appl. No.: 13/387,753

(22) PCT Filed: Jul. 29, 2010

(86) PCT No.: PCT/JP2010/062744
§ 371 (c)(1),
(2), (4) Date: Jan. 30, 2012

(87) PCT Pub. No.: WO2011/016376
PCT Pub. Date: Feb. 10, 2011

(65) Prior Publication Data
US 2012/0128588 A1 May 24, 2012

(30) Foreign Application Priority Data

Aug. 3, 2009 (JP) ................................. 2009-181122

(51) Int. Cl.
*A61K 51/00* (2006.01)
*A61M 36/14* (2006.01)
*A61K 31/192* (2006.01)
*A61K 49/04* (2006.01)
*A61K 51/04* (2006.01)

(52) U.S. Cl.
CPC ........... *A61K 31/192* (2013.01); *A61K 49/0433* (2013.01); *A61K 51/0402* (2013.01)
USPC ....................................................... 424/1.11

(58) Field of Classification Search
USPC ....................................................... 424/1.11
See application file for complete search history.

(56) References Cited

U.S. PATENT DOCUMENTS

2006/0263293 A1 11/2006 Kolb et al.
2010/0029704 A1 2/2010 Hanma et al.

FOREIGN PATENT DOCUMENTS

JP  2008-540338 A  11/2008
WO  WO 2006/116629 A2  11/2006
WO  WO 2008/093686 A1  8/2008

OTHER PUBLICATIONS

Elder, "Synthesis and in vivo distribution of a non-steroidal antiinflammatory drug: 18F-flurbiprofen," Dissertation from Diss. Abstr. Int. B, University Microfilms International, Order No. 9129898, Cover sheets, Abstract, Acknowledgements, Table of Contents plus pp. 1 to 155, Mar. 12, 1991.
Fujisaki et al., "Radiosynthesis and in vivo evaluation of 11C-labeled 1,5-diarylpyrazole derivatives for mapping cyclooxygenases," Annals of Nuclear Medicine, 2005, vol. 19, No. 7, pp. 617 to 625.
Gao et al., "Synthesis of carbon-11 labeled celecoxib derivatives as new candidate Pet redioligands for imaging of inflammation," Applied Radiation and Isotopes, vol. 67, 2009, pp. 2019 to 2024.
Hirohata et al., "Anti-amyloidogenic Effects of Non-steroidal Anti-inflammatory Drugs: Novel Therapeutic and Preventative Opportunities for Alzheimer's Disease," Neurological Therapeutics, 2007, vol. 24, No. 2, pp. 187 to 194.
International Search Report issued in PCT/JP2010/062744, dated Oct. 19, 2010.
Majo et al., "A general method for the synthesis of aryl [11C]methylsulfones: Potential PET probes for imaging cyclooxygenase-2 expression," Bioorganic & Medicinal Chemistry Letters, vol. 15, 2005, pp. 4268 to 4271.
McCarthy et al., "Radiosynthesis, In Vitro Validation, and In Vivo Evaluation of 18F-Labeled COX-1 and COX-2 Inhibitors," J Nucl Med, 2002, No. 43, vol. 1, pp. 117 to 124.
Miller et al., "Synthesis of 11C, 18F, 15O, and 13N Radiolabels for Positron Emission Tomography," Angew. Chem. Int. Ed., 2008, vol. 47, pp. 8998 to 9033.
Ogawa et al., "Malonic Ester and Acetoacetic Ester Synthesis of 2-[11,14C]Methyl-fatty Acids," Appl. Radiat. Isol., 1997, vol. 48, No. 5, pp. 623 to 630.
Prabhakaran et al., "Synthesis and in vivo evaluation of [18F]-4-[5-(4-methylphenyl)-3-(trifluoromethyl)-1H-pyrazol-1-yl]benzenesulfonamide as a PET imaging probe for It for COX-2 expression," Bioorganic & Medicinal Chemistry, vol. 15, 2007, pp. 1802 to 1807.
Prabhakaran et al., "Synthesis of [11C]celecoxib: a potential PET probe for imaging COX-2 expression," J Label Compd Radiopharm, 2005, vol. 48, pp. 887 to 895.

(Continued)

*Primary Examiner* — Michael G Hartley
*Assistant Examiner* — Melissa Perreira
(74) *Attorney, Agent, or Firm* — Birch, Stewart, Kolasch & Birch, LLP

(57) ABSTRACT

Disclosed are: labeled NSAIDs compounds which can be produced within a short time, can be used suitably for a PET method, and enable the imaging of cyclooxygenase-2; and a process for producing the labeled NSAIDs compounds. Specifically disclosed are isotope-labeled 2-arylpropionic acid compounds, each of which is a compound represented by general formula (1) (wherein Ar represents an aryl group which may have a substituent; $R^1$ represents anyone selected from $^{11}CH_3$, $CH_2^{18}F$ and $CF_2^{18}F$; and $R^2$ represents a hydrogen atom, or an alkyl group which may have a branch, wherein a compound wherein Ar is a benzene ring, $R^1$ is $^{11}CH_3$, and $R^2$ is a hydrogen atom is excluded), or a pharmaceutically acceptable salt, hydrate, solvate or prodrug thereof.

8 Claims, 25 Drawing Sheets

(56) References Cited

OTHER PUBLICATIONS

Sasaki et al., "Synthesis of [11C]salicylic acid and related compounds and their biodistribution in mice," Applied Radiation and Isotopes, vol. 50, 1999, pp. 905 to 909.

Tanaka et al., "Radiosynthesis and Evaluation of 11C-Labeled Diaryl-Substituted Imidazole and Indole Derivatives for Mapping Cyclooxygenase-2," Biol. Pharm. Bull., vol. 29, 2006, No. 10, pp. 2087 to 2094.

Vries et al., "Evaluation of [11C]rofecoxib as PET tracer for cyclooxygenase 2 overexpression in rat models of inflammation," Nuclear Medicine and Biology, vol. 35, 2008, pp. 35 to 42.

Vries et al., "Synthesis and In Vivo Evaluation of 18F-Desbromo-DuP-697 as a PET Tracer for Cyclooxygenase-2 Expression," The Journal of Nuclear Medicine, Oct. 2003, vol. 44, No. 10, pp. 1700 to 1706.

Wuest et al., "Synthesis and evaluation in vitro and in vivo of a 11C-labeled cyclooxygenase-2(COX-2) inhibitor," Bioorganic & Medicinal Chemistry, vol. 16, 2008, pp. 7662 to 7670.

Wust et al., "Synthesis of 18F-labelled cyclooxygenase-2 (COX-2) inhibitors via Stille reaction with 4-[18F]Fluoroiodobenzene as radiotracers for positron emission tomography (PET)," Org. Biomol. Chem., 2005, vol. 3, pp. 503 to 507.

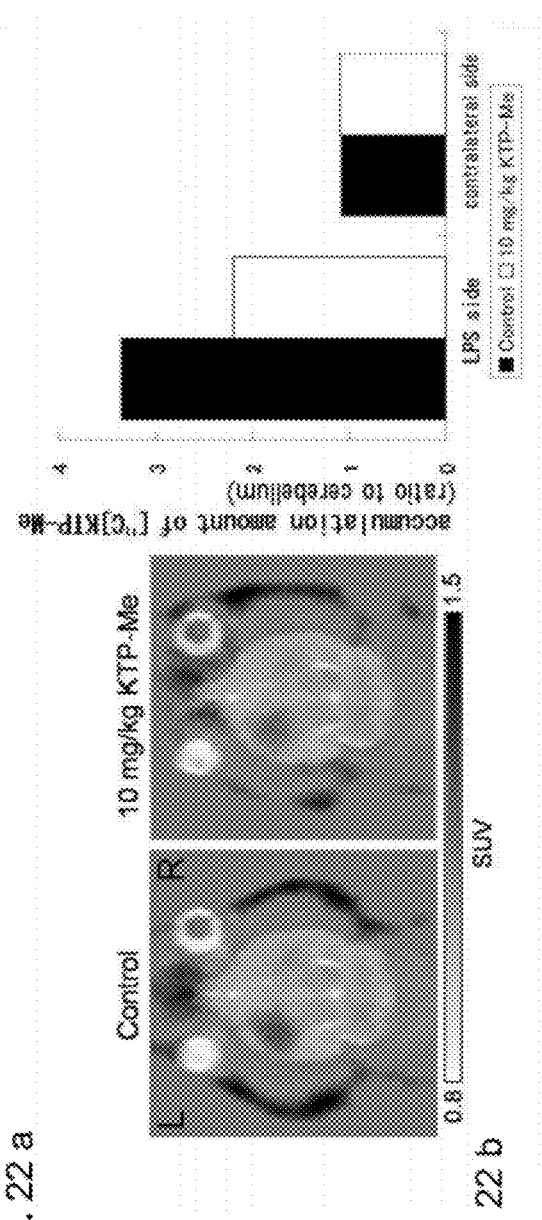
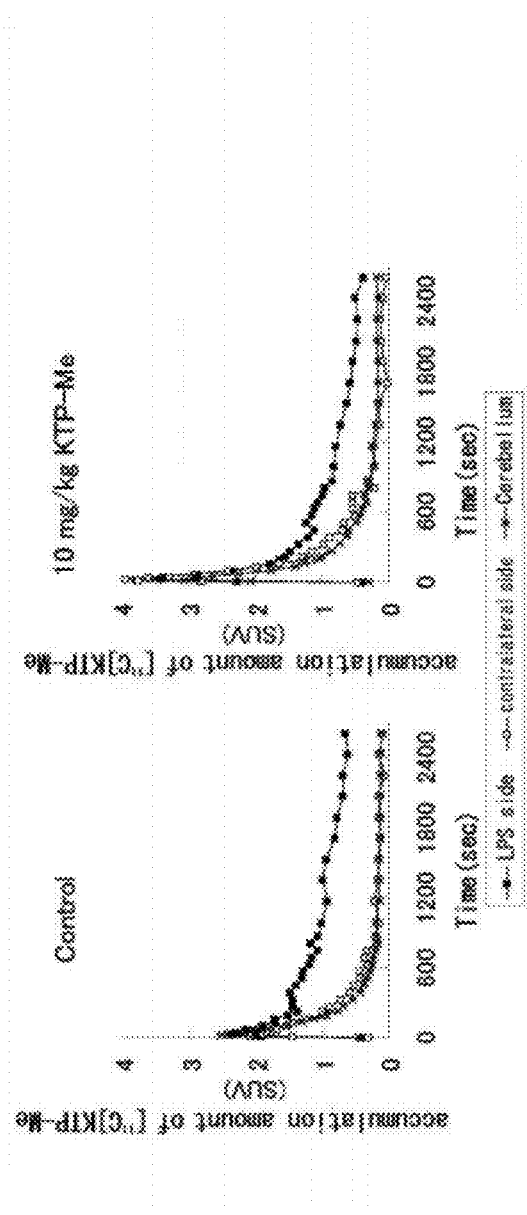
FIG. 22 a
FIG. 22 b

ISOTOPE LABELED 2-ARYLPROPIONIC ACID COMPOUNDS AND PROCESS FOR PRODUCTION OF SAME, AND MOLECULAR PROBE FOR POSITRON EMISSION TOMOGRAPHY AND METHOD FOR IMAGING OF CYCLOOXYGENASE AND THE LIKE USING SAME

TECHNICAL FIELD

The present invention relates to an isotope-labeled 2-arylpropionic acid compounds and a process for producing the same and a molecular probe for positron emission tomography (hereinafter referred to as "PET") and a method for imaging of cyclooxygenase using the molecular probe. The isotope-labeled 2-arylpropionic acid compounds and the process for producing the same of the present invention are preferably used as a molecular probe used in positron emission tomography (hereinafter referred to as "PET method") and a process for producing the same. Imaging of cyclooxygenase can be performed by using the molecular probe of the present invention.

BACKGROUND ART

Many of non-steroidal anti-inflammatory drugs that have been widely used as antipyretic, analgesic and agents for antiinflammatory (hereinafter referred to as "NSAIDs") show pharmacologic actions mainly by inhibiting an enzyme called cyclooxygenase. Cyclooxygenase is involved in enormous numbers of pathologic conditions such as pain, fever, chronic and acute inflammation, arthritis, colon cancer, new blood vessel growth, asthma, arterial sclerosis, Alzheimer disease, and Parkinson's disease. Therefore, it has been considered that examining behaviors of NSAIDs within a living body makes it possible to find out many pathologic conditions and diagnoses.

According to the above described reasons, examining behaviors of NSAIDs in the living body by a PET method has been actively tried in recent years. PET is a method that includes administering, into a living body, a tracer labeled with a short-term radionuclide which releases positrons such as $^{11}C$ or $^{18}F$ so that γ rays generated from the tracer is measured by a PET camera (detector comprising a gamma ray scintillator and a photoelectron multiplier tube), and imaging a body distribution of the γ ray by a computer. The PET method can non-invasively and quantitatively track down behaviors of medical agents in living bodies including from small animals to a human and a degree of reaching a target site. NSAIDs such as ibuprofen and naproxen inhibit functions of an enzyme called cyclooxygenase in a living body to show anti-inflammatory actions, and it was found that cyclooxygenase is involved in not only inflammation but also tumors, Alzheimer disease, and the like. Therefore, in order to apply NSAIDs to a PET method, numerous NSAIDs have been labeled with $^{11}C$ and $^{18}F$ (Non-Patent Documents 1 to 15). Analyzing PET images for NSAIDs enables non-invasive imaging of cyclooxygenase, and consequently, significantly useful information can be obtained in respective fields such as biology, development of pharmaceutical products, and medical services.

PRIOR ART DOCUMENTS

Patent Documents

Patent Document 1: WO2006/116629

Non-Patent Documents

Non-Patent Document 1: Phillip W. Miller, Nicholas J. Long, Ramon Vilar, Antony D. Gee, Synthesis of 11C, 18F, 15O, and 13N Radiolabels for Positron Emission Tomography. Angew. Chem. Int. Ed. 2008, 47, 8998-9033.

Non-Patent Document 2: Toru Sasaki, Koji Ogawa, Shin-Ichi Ishii, Michio Senda, Synthesis of [11C]salicylic acid and related compounds and their biodistribution in mice. Applied Radiation and Isotopes, 1999, 50, 905-909.

Non-Patent Document 3: Elder, Stewart Todd, Synthesis and in vivo distribution of a nonsteroidal anti-inflammatory drug: fluorine-18-labeled flurbiprofen. Univ. Kentucky, Lexington, Ky., USA. Avail. Univ. Microfilms Int., Order No. DA9129898. (1991), 176 pp. From: Diss. Abstr. Int. B 1991, 52(5), 2566.

Non-Patent Document 4: Jaya Prabhakaran, Vattoy J. Majo, Norman R. Simpson, Ronald L. Van Heertum, J. John Mann, J. S. Dileep Kumar, Synthesis of [11C]celecoxib: a potential PET probe for imaging COX-2 expression, J. Label. Compd. Radiopharm. 2005, 48, 887-895.

Non-Patent Document 5: Jaya Prabhakaran, Mark D. Underwood, Ramin V. Parsey, Victoria Arango, Vattoly J. Majo, Norman R. Simpson, Ronald Van Heertum, J. John Mann, J. S. Dileep Kumar, Synthesis and in vivo evaluation of [18F]-4-[5-(4-methylphenyl)-3-(trifluoromethyl)-1H-pyrazol-1-yl]benzenesulfonamide as a PET imaging probe for COX-2 expression, Bioorg. Med. Chem. 2007, 15, 1802-1807.

Non-Patent Document 6: Erik F. J. Vries, Janine Doorduin, Rudi A. Dierckx, Aren van Waard, Evaluation of [11C] Rofecoxib as PET tracer for cyclooxygenase 2 overexpression in rat models of inflammation, Nucl. Med. Biol. 2008, 35, 35-42.

Non-Patent Document 7: Vattoly J. Majo, Jaya Prabhakaran, Norman R. Simpson, Ronald L. Van Heertum, J. John Mann, J. S. Dileep Kumar, A general method for the synthesis of aryl[11C]methylsulfones: Potential PET probes for imaging cyclooxygenase-2 expression, Bioorg. Med. Chem. Lett. 2005, 15, 4268-4271.

Non-Patent Document 8: Yoshihiko Fujisaki, Kazunori Kawamura, Wei-Fang Wang, Kiichi Ishiwata, Fumihiko Yamamoto, Takashi Kuwano, Mayumi Ono, Minoru Maeda, Radiosynthesis and in vivo evaluation of 11C-labeled 1,5-diarylpyrazole derivatives for mapping cyclooxygenase, Annal. Nucl. Med. 2005, 19, 617-625.

Non-Patent Document 9: Mariko Tanaka, Yoshihiko Fujisaki, Kazunori Kawamura, Kiichi Ishiwata, Qinggeletu, Fumihiko Yamamoto, Takahiro Mukai, Minoru Maeda, Radiosynthesis and Evaluation of 11C-Labeled Diaryl-Substituted Imidazole and Indole Derivatives for Mapping Cyclooxygenase-2, Biol. Pharm. Bull. 2006, 29, 2087-2094.

Non-Patent Document 10: Timothy J. McCarthy, Ahmed U. Sheriff, Matthew J. Graneto, John J. Talley, Michael J. Welch, Radiosynthesis, in vitro validation, and in vivo evaluation of 18F-Laveled COX-1 and COX-2 inhibitors, J. Nucl. Med. 2002, 43, 117-124.

Non-Patent Document 11: Erik F. J. Vries, Aren van Waarde, Anne Rixt Buursma, Willem Vaalburg, Synthesis and in vivo evaluation of 18F-Desbromo-Dup-697 as a PET tracer for cyclooxygenase-2 Expression, J. Nucl. Med. 2003, 44, 1700-1706.

Non-Patent Document 12: Frank Wuest, Torsten Kniess, Ralf Bergmann, Jens Pietzsch, Synthesis and evaluation in vitro and in vivo of a 11C-labeled cyclooxygenase-2 (COX-2) inhibitor, Bioorg. Med. Chem. 2008, 16, 7662-7670.

Non-Patent Document 13: Frank R. Wust, aileen Hohne, Peter Metz, Synthesis of 18F-labelled cyclooxygenase-2 (COX-2) inhibitors via Stille reaction with 4-[18F]fluoroiodobenzene as radiotracers for positron emission tomography (PET), Org. Biomol. Chem. 2005, 3, 503-507.

Non-Patent Document 14: Koji Ogawa, Motoji Sasaki, Tadashi Nozaki, Applied Radiation and Isotopes, 1997, 48, 623-630.

Non-Patent Document 15: MingzhangGao, Min Wang, Kathy D. Miller, Gary D. Hutchins and Qi-Huang Zheng, Synthesis of carbon-11 labeled celecoxib derivatives as new candidate PET radioligands for imaging of inflammation, Appl. Radiat. Isot. 2009, 67, 2019-2024.

SUMMARY OF THE INVENTION

Problem to be Solved by the Invention

As described above, examining behaviors of NSAIDs in a living body by a PET method has been tried in all over the world. However, although some compounds have been observed to accumulate in an inflammation site and tumor site so far, it cannot be demonstrated that such compounds form bonds specific to cyclooxygenase.

As described above, a cause of not obtaining a satisfactory PET image for behaviors of NSAIDs in a living body so far includes time restriction. That is, examples of the short-term radionuclide used in the PET are $^{11}$C and $^{18}$F, and compounds labeled with these radionuclides are used as the tracer. There is a very broad application range for the $^{11}$C utilizing carbon atoms present in organic compounds, therefore, $^{11}$C can be considered to be an ideal radionuclide. However, the $^{11}$C has such a short half-life as 20 minutes, and the process from synthesis through the PET method must be completed within a very short time frame. Further, $^{18}$F having a half-life longer than that of the $^{11}$C, 110 minutes, however, the process from synthesis through the PET method must be completed within a very short time frame. Due to difficulty such as time restriction, restriction was added to a synthesis method, and the number and kind of a labeling compound to be synthesized, satisfactory PET image for behaviors of NSAIDs cannot be obtained up to the present date regardless of many trials made in all over the world.

The present invention was accomplished to solve the above described conventional problems, and an object of the present invention is to provide a labeled NSAIDs compound that can be produced in a short time, preferably used in a PET method, and is capable of imaging cyclooxygenase, and a process for producing the same.

Means for Solving the Problem

To solve the conventional problems, the inventors of the present invention focused on NSAIDs, 2-arylpropionic acids, such as ibuprofen, naproxen, etc. and the derivatives. As the results, the inventors succeeded in the introduction of [$^{11}$C] methyl group into the corresponding arylacetic acid in a short time and the purification. Furthermore, when a PET method is performed using the isotope-labeled 2-arylpropionic acid compounds as tracers, a labeled medical agent accumulated in an expression site of cyclooxygenase and the present inventors succeeded in showing a specific binding for the first time in the world.

That is, the isotope-labeled 2-arylpropionic acid compounds of the present invention are characterized by including a compound represented by the following general formula (1) (wherein Ar represents an aryl group which may have a substituent; $R^1$ represents any one of $^{11}CH_3$, $CH_2^{18}F$ and $CF_2^{18}F$; and $R^2$ represents a hydrogen atom, or an alkyl group which may have a branch, provided that a compound wherein Ar is a benzene ring, $R^1$ is $^{11}CH_3$, and $R^2$ is a hydrogen atom is excluded), or a pharmaceutically acceptable salt, hydrate, solvate or prodrug thereof:

[Chemical Formula 1]

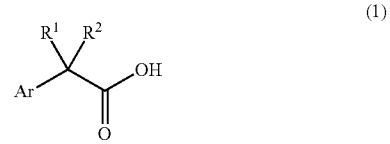

(1)

In the isotope-labeled 2-arylpropionic acid compounds of the present invention, isotope-labeled $R^1$ is introduced into a carbon atom interposed between a carbonyl group and an aryl group that are electron attractive groups. Therefore, isotope-labeled $R^1$ can be easily introduced through a carboanion from a precursor in which $R^1$ is a hydrogen atom in the general formula (1). In addition that this reaction proceeds in a moment of time, ester hydrolysis is completed within 1 minute, and synthesis can be thus completed in a short time though it is two-step synthesis. Therefore, a ratio of the radioactivity decaying with synthetic time is small, and the isotope-labeled 2-arylpropionic acid compounds can be used as molecular probes effective to a PET method.

In addition, $R^2$ is preferably an alkyl group having 1 to 6 carbon atoms.

The isotope-labeled 2-arylpropionic acid compounds of the present invention include a salt, hydrate, solvate, and prodrug in addition to carboxylic acid. Herein, the prodrug is referred to as a compound that is hydrolyzed in a living body to generate the isotope-labeled 2-arylpropionic acid of the present invention. The prodrug of the present invention includes compounds produced in all techniques for forming prodrugs, which are known to a person skilled in the art. For example, in the case of having a carboxyl group or an amino group, a compound obtained by inducing one of the carboxyl group or amino group to an ester group, an amide group, or the like, which could be easily hydrolyzed in the living body corresponds to a prodrug. Specific examples include compounds obtained by inducing a carboxyl group that is present in isotope-labeled 2-arylpropionic acid into alkyl such as methyl and ethyl, alkyloxyalkyl such as methyloxymethyl, ethyloxymethyl, 2-methyloxyethyl and 2-methyloxyethyloxymethyl, acyloxymethyl such as pivaloyloxymethyl, acetyloxymethyl, cyclohexylacetyloxymethyl and 1-methylcyclohexylcarbonyloxymethyl, alkoxycarbonylalkyl such as ethyloxycarbonyloxy-1-ethyl, and cycloalkyloxycarbonylalkyl such as cyclohexyloxycarbonyloxy-1-ethyl. When an aryl group has an amino group, an example includes a compound obtained by inducing the amino group to an acetoamide, or the like.

Examples of pharmaceutically acceptable salts include base addition salts and acid addition salts. Examples of the base addition salts include inorganic basic salts such as sodium salt and calcium salt, and organic basic salts such as meglumine salt, and trishydroxymethylaminomethane salt. Examples of the acid addition salts include, for example, inorganic acid salts such as hydrochloride, hydrobromide, phosphate, sulfate and nitrate, and organic acid salts such as formate, acetate, propionate, maleate, fumarate, succinate, lactate, malate, tartrate, citrate, ascorbate, malonate, oxalate, glycolate, phthalate and benzene sulfonate, and combination of the above described salts can be also used.

$R^1$ can be $^{11}CH_3$.

The isotope-labeled 2-arylpropionic acid compounds of the present invention can be rapidly and simply synthesized in the following method. That is, a process for producing the isotope-labeled 2-arylpropionic acid compounds of the present invention is characterized by having a carboanion generation step of adding a base to a 2-arylacetic acid ester represented by the following general formula (2) (wherein Ar represents an aryl group which may have a substituent; $R^2$ represents a hydrogen atom, or an alkyl group which may have a branch; and $R^3$ represents a hydrogen atom, an alkyl group which may have a substituent, or an aryl group which may have a substituent) to be mixed, and an isotope labeling introduction step of adding any one of $^{11}CH_3X$, $CH_2^{18}FX$ and $CF_2^{18}FX$ (wherein X represents any of I, Br and a triflate group) to the reaction solution after the carboanion generation step:

[Chemical Formula 2]

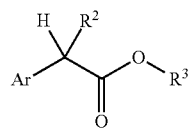

(2)

In the process for producing the isotope-labeled 2-arylpropionic acid compounds of the present invention, a base is added to a 2-arylacetic acid ester represented by the above general formula (2) and mixed in the carboanion generation step. Examples of a substituent of $R^3$ include a halogen atom, a carboxyl group, an ester group, a hydroxyl group, a thiol group and an alkoxy group. When $R^3$ is an alkyl group, a preferable substituent is an alkyl group having 6 to 10 carbon atoms. When $R^3$ is an aryl group, a preferable substituent is an aryl group having 6 to 10 carbon atoms. For a solvent, anhydrous N,N-dimethyl formamide (DMF), anhydrous tetrahydrofuran, and the like can be used. For a base, sodium hydride, potassium hydride, lithium diisopropylamide, sodium bis(trimethylsilyl)amide, lithium bis(trimethylsilyl)amide, and the like can be used. Thereby, active hydrogen that is bound to a carbon atom interposed between an aryl group and a carbonyl group is detached to generate carboanion. Then, any one of $^{11}CH_3X$, $CH_2^{18}FX$ and $CF_2^{18}FX$ is added to the reaction solution in the isotope labeling introduction step. These labeling compounds can be easily synthesized by chemical change from nuclear species that are generated in a cyclotron. Thereby, any one of $^{11}CH_3$, $CH_2^{18}F$ and $CF_2^{18}F$ is introduced in place of a hydrogen atom in a benzyl position.

In addition, when a hydrolysis reaction is further carried out, corresponding carboxylic acid can be obtained.

FIG. 2 in Non-Patent Document 13 shows an idea of introduction of $^{11}CH_3$ using a technique of synthesis of an acetoacetic acid ester, a step of decarboxylation, and the like are required so that the number of steps are large, and production of the isotope-labeled 2-arylpropionic acid compounds of the present invention by this method requires time as well as complicated operations; therefore, application to a PET method is difficult.

Furthermore, though [$^{18}F$]flurbiprofen is synthesized in Non-Patent Document 3, the method of the present invention can label a common moiety of large numbers of 2-arylpropionic acid compounds in the same method and thus is considered to be a method having a wide range of applications.

The isotope-labeled 2-arylpropionic acid compounds of the present invention can be preferably used as molecular probes for PET. The present inventors applied the isotope-labeled 2-arylpropionic acid compounds of the present invention to a PET method, thereby confirming capability of imaging of cyclooxygenase and imaging of brain inflammation that is involved in neurodegeneration in Alzheimer disease.

BEST MODE FOR CARRYING OUT THE INVENTION

Examples of NSAIDs having analogical structures to the isotope-labeled 2-arylpropionic acid compounds of the present invention include compounds having the following structural formulas and names.

[Chemical Formula 3]

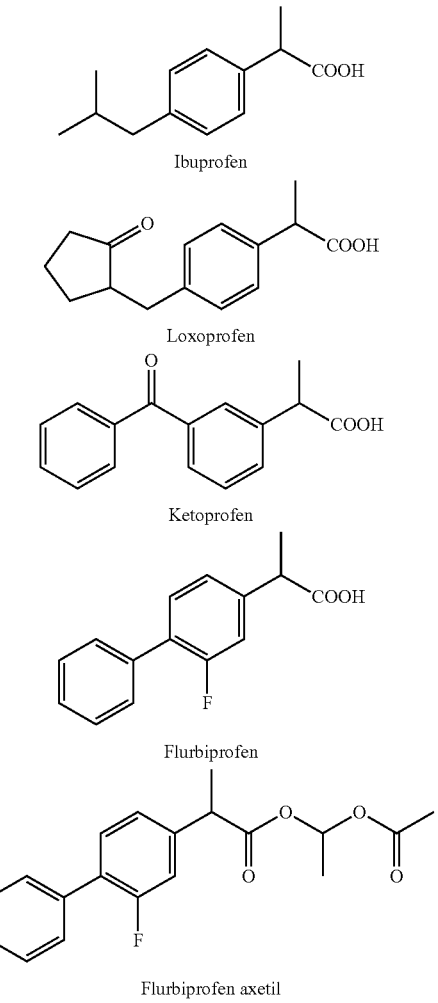

Ibuprofen

Loxoprofen

Ketoprofen

Flurbiprofen

Flurbiprofen axetil

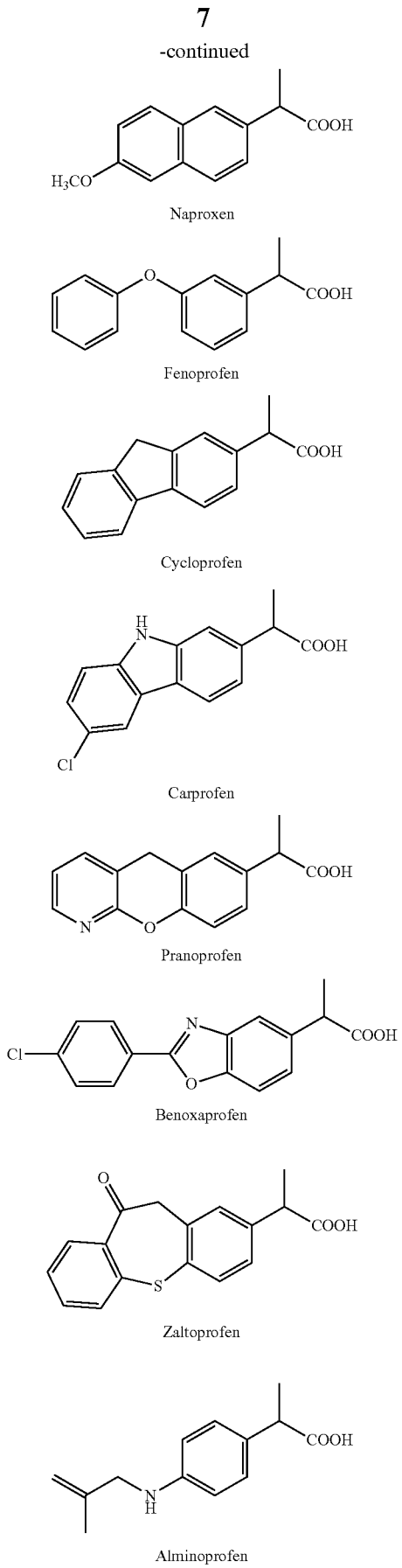

Naproxen

Fenoprofen

Cycloprofen

Carprofen

Pranoprofen

Benoxaprofen

Zaltoprofen

Alminoprofen

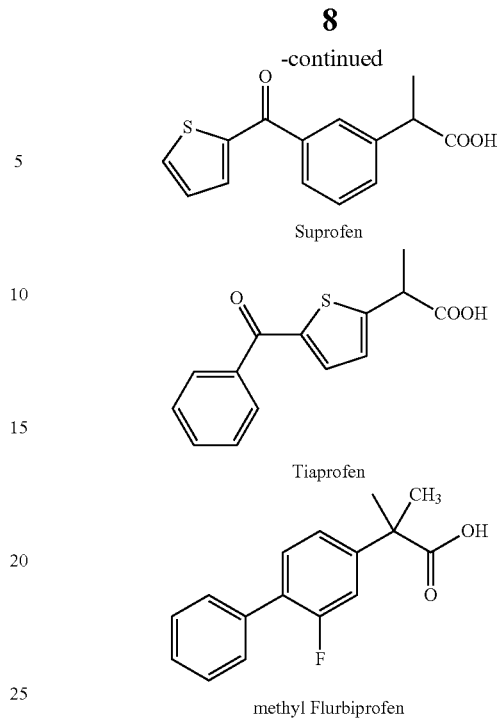

Suprofen

Tiaprofen methyl Flurbiprofen

Compounds obtained by substituting methyl groups in benzyl positions with any one of $^{11}CH_3$, $CH_2{}^{18}F$ and $CF_2{}^{18}F$ are included in the isotope-labeled 2-arylpropionic acid compounds of the present invention. Taking PET images of the isotope-labeled 2-arylpropionic acid compounds of the present invention imitating NSAIDs makes it possible to examine behaviors of the NSAIDs over time in a living body.

In addition, an ester form can be also used as a prodrug of isotope-labeled 2-arylpropionic acid. Converting to an ester form enables a brain transfer property to improve more than administering in a form of carboxylic acid, and imaging of an inflammation site in the brain can be carried out as described below in examples.

The isotope-labeled 2-arylpropionic acid compounds of the present invention can be obtained in the following reaction.

[Chemical Formula 4]

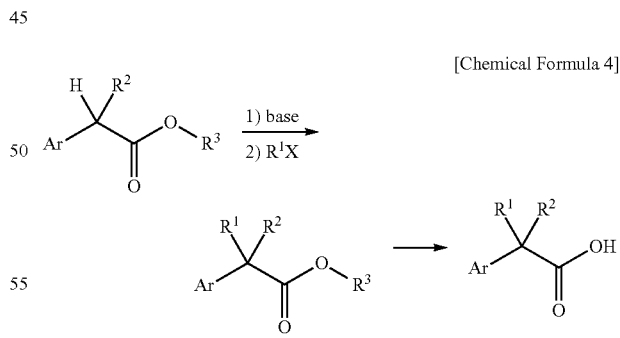

That is, a 2-arylacetic acid ester having a hydrogen atom in a benzyl position is used as a precursor and the hydrogen atom in the benzyl position is drawn with a base to form carboanion. Then, the carboanion is reacted with $R^1X$ (herein, $R^1$ represents any one of $^{11}CH_3$, $CH_2{}^{18}F$ and $CF_2{}^{18}F$, and X represents any of I, Br and a triflate group) to introduce $R^1$ into a benzyl position, and the reaction product is further hydrolyzed with alkali, or the like to thus obtain the isotope-labeled 2-arylpropionic acid of the present invention. When a functional group having active hydrogen, such as an amino group and a hydroxyl group, is present in an aryl group, a protection and deprotection step described in Protective Groups in Organic Synthesis (T. W. Green, et al.) can be utilized. Hydrolysis in a final step may not be performed in the case of an ester type for a desired isotope-labeled 2-arylpropionic acid compound. An administration solution of an isotope-labeled 2-arylpropionic acid compound finally obtained can be prepared by dissolving into a solvent obtained by adding ethylene glycol, ethanol, Tween 80, ascorbic acid, cyclodextrin, etc. to saline.

Examples specifying the present invention will be described in detail in the following.

[Reagents and Solvents]

Commercially available products were directly used for all chemical reagents and NSAIDs unless otherwise specified. Heavy chloroform and heavy dimethyl sulfoxide were used for measurement solvents of NMR spectra. Commercially available products of ethyl acetate, hexane, dichloromethane and methanol were directly used for extraction and elution solvents of chromatography.

[Labeling Reaction]

The $^{11}C$ is produced by $^{14}N(p,\alpha)^{11}C$ nuclear reaction using CYPRIS HM-12S Cyclotron manufactured by Sumitomo Heavy Industries, Ltd. A series of procedures including preparation of [$^{11}C$]methyl iodide ([$^{11}C$]CH$_3$I), heating and dilution of the reaction solution, injection into the high performance liquid chromatography (HPLC) apparatus, preparative separation, concentration, and sterilization were performed using an originally-developed automatic synthesizer. The preparative HPLC was performed using LC-2000 manufactured by JASCO Corporation. The analytical HPLC was performed using Prominence manufactured by Shimadzu Corporation. The emitted radioactivity was measured using RLC-700 Radioanalyzer manufactured by ALOKA CO., LTD. COSMOSIL manufactured by NACALAI TESQUE, INC. is used for the HPLC column, and a column manufactured by Daicel Corporation was used for the chiral column.

[Spectrometer]

For $^1$H NMR spectra, tetramethylsilane (TMS) was used as the internal standard substance, and the $^1$H NMR spectra were measured using JEOL JNM-AL-400 (400 MHz) FT-NMR manufactured by JEOL Ltd. A chemical shift δ value was expressed by ppm. A chemical association constant (J) was expressed by Hz, and for breakup manners of signals, single line was abbreviated as s, double line was abbreviated as d, triple line was abbreviated as t, quadruple line was abbreviated as q, multiple line was abbreviated as m, and broad line was abbreviated as br.

Example 1

Synthesis of [$^{11}C$]Ibuprofen (3)

[Chemical Formula 5]

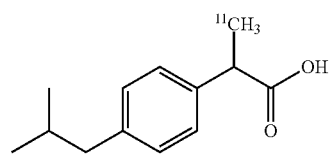

(3)

Under an argon atmosphere, sodium hydride (1 mg) was added to an anhydrous DMF (200 μL) solution of methyl 2-(4-isobutylphenyl)acetate (EP347939) (1 mg) and stirred. Then, immediately after capturing [$^{11}C$]CH$_3$I at room temperature, thereto was added 2 M sodium hydroxide (300 μL). The obtained reaction solution was heated at 50° C. for 1 minute, the reaction was ceased with an acetonitrile solution (300 μL) of 10% formic acid, and the mixed solution was then diluted with a solution made of acetonitrile (150 μL), water (150 μL), and 25% ascorbic acid (50 μL). The reaction mixture thus obtained was separated by preparative HPLC (mobile phase; acetonitrile: 10 mM sodium phosphate buffer (pH 7.4)=34:66, column; COSMOSIL, 5C$_{18}$-MS-II, inner diameter 20 mm×length 250 mm, particle diameter 5 μm, flow rate; 10 mL/min, UV detector; 195 nm). As a result, [$^{11}C$]ibuprofen (3) was eluted at a retention time of 19 to 20 minutes as shown in FIG. 1. A target fraction was concentrated under a reduced pressure using an evaporator, and thereto was added a diluting solution made of saline (4.0 mL), propylene glycol (0.3 mL), Tween 80 (0.05 mL), and 25% ascorbic acid (0.2 mL) to form a solution for administration.

A radioactivity was 4.95 GBq on completion of the reaction, and a specific radioactivity was 34 GBq/μmol. An isolated yield after decay-corrected based on [$^{11}C$]CH$_3$I was 69%. A total time for synthesis and separation of [$^{11}C$]ibuprofen (3), and preparation of an intravenous injection solution was about 37 minutes. An authentic sample of ibuprofen was mixed and a result of analytical HPLC showed a single peak, thereby determining identification of the [$^{11}C$]ibuprofen (3) (mobile phase; acetonitrile: aqueous 1% phosphoric acid solution=60:40, column; COSMOSIL, 5C$_{18}$-MS-II, inner diameter 4.6 mm×length 150 mm, particle diameter 5 μm, flow rate; 1 mL/min, UV detector; 210 nm). As a result, a retention time was about 6 minutes, and a purity was 99% or more.

Example 2

Synthesis of [$^{11}C$]Ibuprofen Methyl Ester (4)

[Chemical Formula 6]

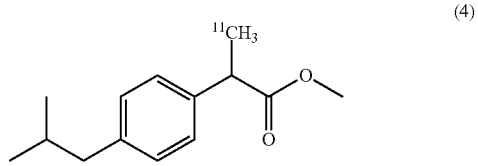

(4)

Under an argon atmosphere, methyl 2-(4-isobutylphenyl)acetate (1 mg) was dissolved in anhydrous DMF (200 μL), and sodium hydride (1 mg) was added thereto and stirred. Then, immediately after capturing [$^{11}C$]CH$_3$I at room temperature, the reaction solution as diluted with a solution made of 25% ascorbic acid (50 μL), acetonitrile (400 μL), and water (400 μL). The reaction mixture thus obtained was separated by preparative HPLC (mobile phase; acetonitrile:water=75:25, column; COSMOSIL, 5C$_{18}$-MS-II, inner diameter 20 mm×length 250 mm, particle diameter 5 μm, flow rate; 10 mL/min, UV detector; 195 nm). As a result, [$^{11}C$]ibuprofen methyl ester (4) was eluted at a retention time of 15 to 16 minutes as shown in FIG. 2.

A radioactivity was 4.00 GBq on completion of the reaction, and a specific radioactivity was 23 GBq/μmol. A total time for synthesis and separation of [¹¹C]ibuprofen methyl ester (4), and preparation of an intravenous injection solution was about 30 minutes. An authentic sample of ibuprofen methyl ester was mixed and a result of analytical HPLC showed a single peak, thereby determining identification of the [¹¹C]ibuprofen methyl ester (4) (mobile phase; acetonitrile:water=60:40, column; COSMOSIL, 5C$_{18}$-AR-II, inner diameter 4.6 mm×length 100 mm, particle diameter 5 μm, flow rate; 1 mL/min, UV detector; 210 nm). As a result, a retention time was about 6 minutes, and a purity was 99% or more.

Example 3

Synthesis of [¹¹C]Naproxen (5)

[Chemical Formula 7]

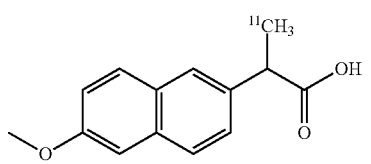

(5)

According to a similar procedure to Example 1, [¹¹C]naproxen (5) was synthetically reacted from methyl 2-(6-methoxynaphthalene-2-yl)acetate (U.S. Pat. No. 3,896,157). The reaction mixture thus obtained was separated by preparative HPLC (mobile phase; acetonitrile: 10 mM sodium phosphate buffer (pH 7.4)=22:78, column; COSMOSIL, 5C$_{18}$-MS-II, inner diameter 20 mm×length 250 mm, particle diameter 5 μm, flow rate; 10 mL/min, UV detector; 200 nm); as a result, [¹¹C]naproxen (5) was eluted at a retention time of 19 to 20 minutes as shown in FIG. 3.

A radioactivity was 3.30 GBq on completion of the reaction, and a specific radioactivity was 29 GBq/μmol. A total time for synthesis and separation of [¹¹C]naproxen (5), and preparation of an intravenous injection solution was about 29 minutes. An authentic sample of naproxen was mixed and a result of analytical HPLC showed a single peak, thereby determining identification of the [¹¹C]naproxen (5) (mobile phase; acetonitrile:aqueous 1% phosphoric acid solution=50:50, column; COSMOSIL, 5C$_{18}$-MS-II, inner diameter 4.6 mm×length 150 mm, particle diameter 5 μm, flow rate; 1 mL/min, UV detector; 254 nm). As a result, a retention time was about 5.2 minutes, and a purity was 99% or more.

Example 4

Synthesis of [¹¹C]Naproxen Methyl Ester (6)

[Chemical Formula 8]

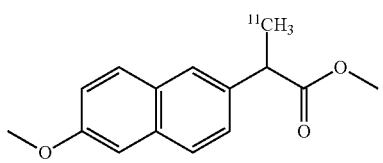

(6)

According to a similar procedure to Example 2, [¹¹C]naproxen methyl ester (6) was synthesized from methyl-2-(6-methoxynaphthalene-2-yl)acetate. The reaction mixture thus obtained was separated by preparative HPLC (mobile phase; acetonitrile:water=65:35, column; COSMOSIL, 5C$_{18}$-MS-II, inner diameter 20 mm×length 250 mm, particle diameter 5 μm, flow rate; 10 mL/min, UV detector; 230 nm); as a result, [¹¹C]naproxen methyl ester (6) was eluted at a retention time of 16.2 minutes as shown in FIG. 4.

A radioactivity was 3.30 GBq on completion of the reaction, and a specific radioactivity was 29 GBq/μmol. A total time for synthesis and separation of [¹¹C]naproxen methyl ester (6), and preparation of an intravenous injection solution was about 32 minutes. An authentic sample of naproxen methyl ester was mixed and a result of analytical HPLC showed a single peak, thereby determining identification of the [¹¹C]naproxen methyl ester (6) (mobile phase; acetonitrile:water=65:35, column; COSMOSIL, 5C$_{18}$-MS-II, inner diameter 4.6 mm×length 150 mm, particle diameter 5 μm, flow rate; 1 mL/min, UV detector; 230 nm). As a result, a retention time was 5.5 minutes, and a purity was 99% or more.

Example 5

Synthesis of [¹¹C]Ketoprofen (7)

[Chemical Formula 9]

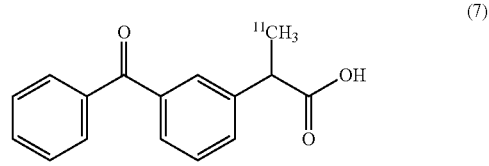

(7)

According to a similar procedure to Example 1, [¹¹C]ketoprofen (7) was synthesized from methyl 2-(3-benzoylphenyl)acetate (Org. Lett. 2002, 4, 3083-3085). The reaction mixture thus obtained was separated by preparative HPLC (mobile phase; acetonitrile: 10 mM sodium phosphate buffer (pH 7.4)=30:70, column; COSMOSIL, 5C$_{18}$-MS-II, inner diameter 20 mm×length 250 mm, particle diameter 5 μm, flow rate; 10 mL/min, UV detector; 254 nm); as a result, [¹¹C]ketoprofen (7) was eluted at a retention time of 14 minutes as shown in FIG. 5.

A radioactivity was 3.40 GBq on completion of the reaction, and a specific radioactivity was 40 GBq/μmol. A total time for synthesis and separation of [¹¹C]ketoprofen (7), and preparation of an intravenous injection solution was about 28 minutes. An authentic sample of ketoprofen was mixed and a result of analytical HPLC showed a single peak, thereby determining identification of the [¹¹C]ketoprofen (7) (mobile phase; acetonitrile:aqueous 1% phosphoric acid solution=40:60, column; COSMOSIL, 5C$_{18}$-AR-II, inner diameter 4.6 mm×length 100 mm, particle diameter 5 μm, flow rate; 1 mL/min, UV detector; 254 nm). As a result, a retention time was 6.8 minutes, and a purity was 99% or more.

Example 6

Synthesis of [$^{11}$C]Ketoprofen Methyl Ester (8)

[Chemical Formula 10]

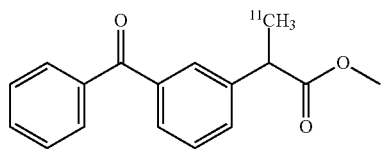

(8)

According to a similar procedure to Example 2, [$^{11}$C]ketoprofen methyl ester (8) was synthesized from methyl 2-(3-benzoylphenyl)acetate. The reaction mixture thus obtained was separated by preparative HPLC (mobile phase; acetonitrile:water=70:30, column; COSMOSIL, 5C$_{18}$-MS-II, inner diameter 20 mm×length 250 mm, particle diameter 5 μm, flow rate; 10 mL/min, UV detector; 254 nm); as a result, [$^{11}$C]ketoprofen methyl ester (8) was eluted at a retention time of 12 minutes as shown in FIG. 6.

A radioactivity was 5.4 GBq on completion of the reaction, and a specific radioactivity was 46 GBq/μmol. A total time for synthesis and separation of [$^{11}$C]ketoprofen methyl ester (8), and preparation of an intravenous injection solution was about 27 minutes. An authentic sample of ketoprofen methyl ester was mixed and a result of analytical HPLC showed a single peak, thereby determining identification of the [$^{11}$C]ketoprofen methyl ester (8) (mobile phase; acetonitrile:water=55:45, column; COSMOSIL, 5C$_{18}$-AR-II, inner diameter 4.6 mm×length 100 mm, particle diameter 5 μm, flow rate; 1 mL/min, UV detector; 254 nm). As a result, a retention time was 6.0 minutes, and a purity was 99% or more.

Example 7

Synthesis of [$^{11}$C]Fenoprofen (9)

[Chemical Formula 11]

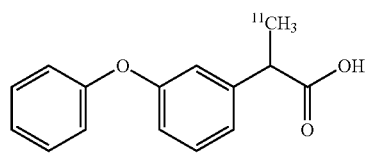

(9)

According to a similar procedure to Example 1, [$^{11}$C]fenoprofen (9) was synthesized from ethyl 2-(3-phenoxyphenyl)acetate (J. Med. Chem. 2005, 48, 995-1018). The reaction mixture thus obtained was separated by preparative HPLC (mobile phase; acetonitrile: 10 mM sodium phosphate buffer (pH 7.4)=20:80, column; COSMOSIL, 5C$_{18}$-MS-II, inner diameter 20 mm×length 250 mm, particle diameter 5 μm, flow rate; 10 mL/min, UV detector; 206 nm); as a result, [$^{11}$C]fenoprofen (9) was eluted at a retention time of 16 minutes as shown in FIG. 7.

A radioactivity was 5.99 GBq on completion of the reaction, and a specific radioactivity was 25 GBq/μmol. A total time for synthesis and separation of [$^{11}$C]fenoprofen (9), and preparation of an intravenous injection solution was about 40 minutes. An authentic sample of fenoprofen was mixed and a result of analytical HPLC showed a single peak, thereby determining identification of the [$^{11}$C]fenoprofen (9) (mobile phase; acetonitrile:aqueous 1% phosphoric acid solution=45:55, column; COSMOSIL, 5C$_{18}$-MS-II, inner diameter 4.6 mm×length 100 mm, particle diameter 5 μm, flow rate; 1 mL/min, UV detector; 220 nm). As a result, a retention time was 8.4 minutes, and a purity was 99% or more.

Example 8

Synthesis of [$^{11}$C]Fenoprofen Methyl Ester (10)

[Chemical Formula 12]

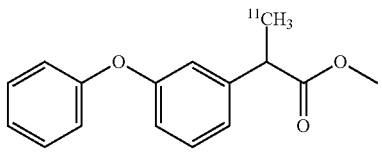

(10)

According to a similar procedure to Example 2, [$^{11}$C]fenoprofen methyl ester (10) was synthesized from methyl 2-(3-phenoxyphenyl)acetate. The reaction mixture thus obtained was separated by preparative HPLC (mobile phase; acetonitrile:water=70:30, column; COSMOSIL, 5C$_{18}$-MS-II, inner diameter 20 mm×length 250 mm, particle diameter 5 μm, flow rate; 10 mL/min, UV detector; 206 nm); as a result, [$^{11}$C]fenoprofen methyl ester (10) was eluted at a retention time of 17 minutes as shown in FIG. 8.

A radioactivity was 4.8 GBq on completion of the reaction, and a specific radioactivity was 43 GBq/μmol. A total time for synthesis and separation of [$^{11}$C]fenoprofen methyl ester (10), and preparation of an intravenous injection solution was about 32 minutes. An authentic sample of fenoprofen methyl ester (Bioorg. Med. Chem. Lett. 2006, 16, 2219-222) was mixed and a result of analytical HPLC showed a single peak, thereby determining identification of the [$^{11}$C]fenoprofen methyl ester (10) (mobile phase; acetonitrile:water=60:40, column; COSMOSIL, 5C$_{18}$-AR-II, inner diameter 4.6 mm×length 100 mm, particle diameter 5 μm, flow rate; 1 mL/min, UV detector; 220 nm). As a result, a retention time was about 5.8 minutes, and a purity was 99% or more.

Example 9

Synthesis of [$^{11}$C]Loxoprofen (11)

[Chemical Formula 13]

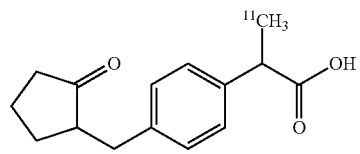

(11)

According to a similar procedure to Example 1, [$^{11}$C]loxoprofen (11) was synthesized from methyl 2-{4-(2-oxocyclopentyl)phenyl}acetate (GB2078732). The reaction mixture thus obtained was separated by preparative HPLC (mobile phase; acetonitrile: 10 mM sodium phosphate buffer (pH 7.4)=20:80, column; COSMOSIL, 5C$_{18}$-MS-II, inner diameter 20 mm×length 250 mm, particle diameter 5 μm, flow rate; 10 mL/min, UV detector; 220 nm); as a result, [$^{11}$C]loxoprofen (11) was eluted at a retention time of 15.9 minutes as shown in FIG. 9.

A radioactivity was 1.9 GBq on completion of the reaction, and a specific radioactivity was 28 GBq/μmol. A total time for synthesis and separation of [$^{11}$C]loxoprofen (11), and preparation of an intravenous injection solution was about 36 minutes. An authentic sample of loxoprofen was mixed and a result of analytical HPLC showed a single peak, thereby determining identification of the [$^{11}$C]loxoprofen (11) (mobile phase; acetonitrile:aqueous 1% phosphoric acid solution=60:40, column; COSMOSIL, 5C$_{18}$-MS-II, inner diameter 4.6 mm×length 150 mm, particle diameter 5 μm, flow rate; 1 mL/min, UV detector; 220 nm). As a result, a retention time was 6.6 minutes, and a purity was 99% or more.

Example 10

Synthesis of [$^{11}$C]Loxoprofen Methyl Ester (12)

[Chemical Formula 14]

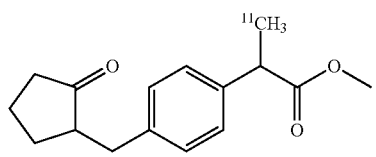

(12)

According to a similar procedure to Example 2, [$^{11}$C]loxoprofen methyl ester (12) was synthesized from methyl 2-{4-(2-oxocyclopentyl)phenyl}acetate. The reaction mixture thus obtained was separated by preparative HPLC (mobile phase; acetonitrile:aqueous 10 mM ammonium formate solution=50:50, column; COSMOSIL, 5C$_{18}$-MS-II, inner diameter 10 mm×length 250 mm, particle diameter 5 μm, flow rate; 6 mL/min, UV detector; 220 nm); as a result, [$^{11}$C]loxoprofen methyl ester (12) was eluted at a retention time of 13 minutes as shown in FIG. 10.

A radioactivity was 2.1 GBq on completion of the reaction, and a specific radioactivity was 33 GBq/μmol. A total time for synthesis and separation of [$^{11}$C]loxoprofen methyl ester (12), and preparation of an intravenous injection solution was about 27 minutes. An authentic sample of loxoprofen methyl ester (FR2483918 A1) was mixed and a result of analytical HPLC showed a single peak, thereby determining identification of the [$^{11}$C]loxoprofen methyl ester (12) (mobile phase; acetonitrile:water=45:55, column; COSMOSIL, 5C$_{18}$-MS-II, inner diameter 4.6 mm×length 150 mm, particle diameter 5 μm, flow rate; 1 mL/min, UV detector; 220 nm). As a result, a retention time was 11.5 minutes, and a purity was 98% or more.

Example 11

Synthesis of [$^{11}$C]Flurbiprofen (13)

[Chemical Formula 15]

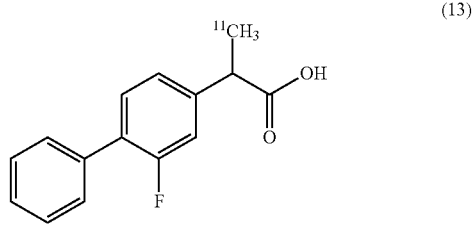

(13)

Methyl 2-(2-fluorobiphenyl-4-yl)acetate (U.S. Pat. No. 3,755,427) was used as a starting material, and [$^{11}$C]flurbiprofen (13) was synthesized according to a method similar to the method of Example 1. The obtained reaction mixture was separated by preparative HPLC (mobile phase; acetonitrile: 10 mM sodium phosphate buffer (pH 7.4)=33:67, column; COSMOSIL, inner diameter 20 mm×length 250 mm, particle diameter 5 μm, flow rate; 10 mL/min, UV detector; 254 nm); as a result, [$^{11}$C]flurbiprofen (13) was eluted at a retention time of 14 to 16 minutes as shown in FIG. 11.

A radioactivity was 3.1 GBq on completion of the reaction, and a specific radioactivity was 76 GBq/μmol.

A total time for synthesis and separation of [$^{11}$C]flurbiprofen (13), and preparation of an intravenous injection solution was about 40 minutes. An authentic sample of flurbiprofen was mixed and a result of analytical HPLC showed a single peak, thereby determining identification of the [$^{11}$C]flurbiprofen (13) (mobile phase; acetonitrile:aqueous 1% phosphoric acid solution=50:50, column; COSMOSIL, inner diameter 4.6 mm×length 100 mm, particle diameter 5 μm, flow rate; 1 mL/min, UV detector; 254 nm). As a result, a retention time was about 6 minutes, and a purity was 99% or more.

Example 12

Synthesis of [$^{11}$C]Flurbiprofen Methyl Ester (14)

[Chemical Formula 16]

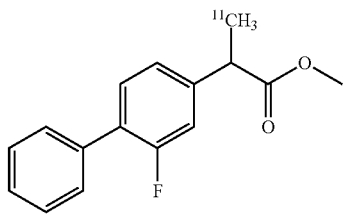

(14)

Methyl 2-(2-fluorobiphenyl-4-yl)acetate was used as a starting material, and [$^{11}$C]flurbiprofen methyl ester (14) was synthesized according to a method similar to the method of Example 2. The obtained reaction mixture was separated by preparative HPLC (mobile phase; acetonitrile:water=75:25, column; COSMOSIL, $5C_{18}$-MS-II, inner diameter 20 mm×length 250 mm, particle diameter 5 μm, flow rate; 10 mL/min, UV detector; 254 nm); as a result, [$^{11}$C]flurbiprofen methyl ester (14) was eluted at a retention time of 15 to 16 minutes as shown in FIG. 12.

A radioactivity was 5.8 GBq on completion of the reaction, and a specific radioactivity was 41 GBq/μmol. A total time for synthesis and separation of [$^{11}$C]flurbiprofen methyl ester (14), and preparation of an intravenous injection solution was about 30 minutes. An authentic sample of flurbiprofen methyl ester was mixed and a result of analytical HPLC showed a single peak, thereby determining identification of the [$^{11}$C]flurbiprofen methyl ester (14) (mobile phase; acetonitrile:water=60:40, column; COSMOSIL, $5C_{18}$-AR-II, inner diameter 4.6 mm×length 100 mm, particle diameter 5 μm, flow rate; 1 mL/min, UV detector; 254 nm). As a result, a retention time was 5.9 to 6.2 minutes, and a purity was 99% or more.

Example 13

Synthesis of (R)—[$^{11}$C]Flurbiprofen (13R) and (S)—[$^{11}$C]Flurbiprofen (13S)

[Chemical Formula 17]

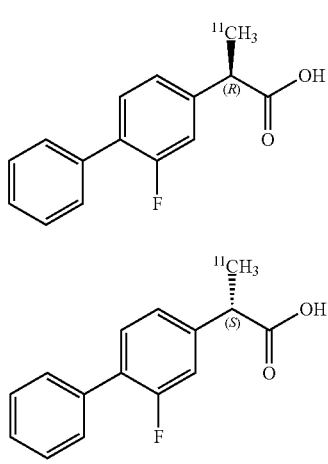

Methyl 2-(2-fluorobiphenyl-4-yl)acetate was used as a starting material, and (R)—[$^{11}$C]flurbiprofen (13R) and (S)—[$^{11}$C]flurbiprofen (13S) were synthesized according to a method similar to the method of Example 1.

Identification of (R)—[$^{11}$C]Flurbiprofen (13R)

The reaction mixture obtained in the above described synthesis reaction was separated by preparative HPLC (mobile phase; 0.05% TFA hexane:0.05% TFA ethanol=95:5, column; CHIRALPAK AD-H, inner diameter 10 mm×length 250 mm, particle diameter 5 μm, flow rate; 3 mL/min, UV detector; 254 nm); as a result, (R)—[$^{11}$C]flurbiprofen (13R) was eluted at a retention time of 10 minutes as shown in FIG. 13. An authentic sample of (R)-flurbiprofen was mixed and a result of analytical HPLC showed a single peak, thereby determining identification of the (R)—[$^{11}$C]flurbiprofen (13R).

Identification of (S)—[$^{11}$C]Flurbiprofen (13S)

On the other hand, the reaction mixture obtained in the above described synthesis reaction was separated by preparative HPLC (mobile phase; 0.05% TFA hexane:0.05% TFA ethanol=95:5, column; CHIRALPAK AD-H, inner diameter 10 mm×length 250 mm, particle diameter 5 μm, flow rate; 3 mL/min, UV detector; 254 nm); as a result, (S)—[$^{11}$C]flurbiprofen (13S) was eluted at a retention time of 13 minutes as shown in FIG. 13. An authentic sample of (S)-flurbiprofen was mixed and a result of analytical HPLC showed a single peak, thereby determining identification of the (S)—[$^{11}$C]flurbiprofen (13S).

Example 14

Synthesis of [$^{11}$C]Flurbiprofen Ethyl Ester (16)

[Chemical Formula 18]

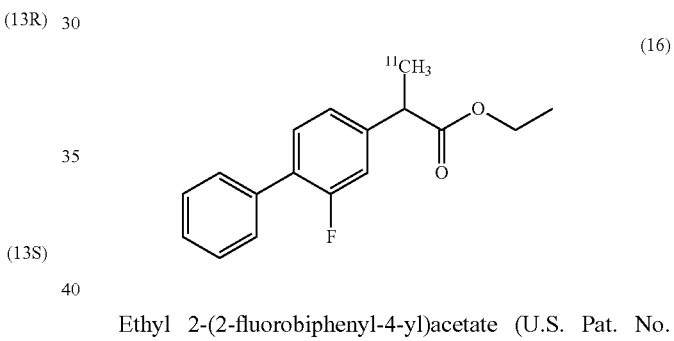

Ethyl 2-(2-fluorobiphenyl-4-yl)acetate (U.S. Pat. No. 3,755,427) was used as a starting material, and [$^{11}$C]flurbiprofen ethyl ester (16) was synthesized according to a method similar to the method of Example 2. The obtained reaction mixture was separated by preparative HPLC (mobile phase; acetonitrile:water=80:20, column; COSMOSIL, $5C_{18}$-MS-II, inner diameter 20 mm×length 250 mm, particle diameter 5 μm, flow rate; 10 mL/min, UV detector; 254 nm); as a result, [$^{11}$C]flurbiprofen ethyl ester (16) was eluted at a retention time of 16 minutes as shown in FIG. 14.

A radioactivity was 4.65 GBq on completion of the reaction, and a specific radioactivity was 42 GBq/μmol. A total time for synthesis and separation of [$^{11}$C]flurbiprofen ethyl ester (16), and preparation of an intravenous injection solution was about 37 minutes. An authentic sample of flurbiprofen ethyl ester (Chem. Pharm. Bull. 1984, 32, 99-105) was mixed and a result of analytical HPLC showed a single peak, thereby determining identification of the [$^{11}$C]flurbiprofen ethyl ester (16) (mobile phase; acetonitrile:water=65:35, column; COSMOSIL, $5C_{18}$-AR-II, inner diameter 4.6 mm×length 100 mm, particle diameter 5 μm, flow rate; 1 mL/min, UV detector; 254 nm). As a result, a retention time was 7.1 minutes, and a purity was 99% or more.

Example 15

Synthesis of [$^{11}$C]Flurbiprofen N-Propyl Ester (17)

[Chemical Formula 19]

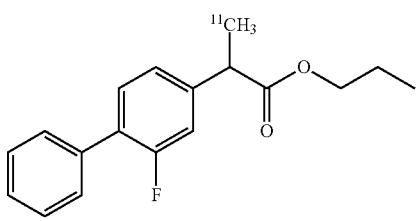

(17)

Step 1

Synthesis of n-propyl 2-(2-fluorobiphenyl-4-yl)acetate (18)

[Chemical Formula 20]

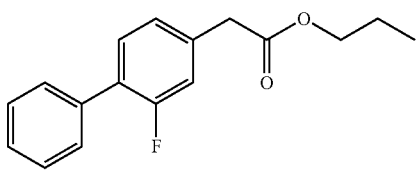

(18)

n-propyl 2-(2-fluorobiphenyl-4-yl)acetate (150 mg, 0.65 mmol) was dissolved into dichloromethane (3 mL), and oxalyl chloride (67 μL, 99 mg, 0.78 mmol) and DMF (10 μL) were added thereto while stirring at room temperature. After stirring for 5 minutes, propanol (97 mL, 78 mg, 1.3 mmol) was added. After stirring further for 5 minutes, the reaction was terminated with water (0.2 mL), and the obtained reaction mixture was separated by silica gel column chromatography (hexane:ethyl acetate=20:1) to thus obtain target n-propyl 2-(2-fluorobiphenyl-4-yl)acetate (18) as a transparent oily substance (yield 84%). The $^1$H NMR spectrum of this substance is shown below.

$^1$H NMR (400 MHz, CDCl$_3$)

δ: 7.55-7.53 (m, 2H), 7.46-7.34 (m, 4H), 7.15-7.10 (m, 2H), 4.09 (t, J=6.8 Hz, 2H), 3.65 (s, 2H), 1.68 (quintet, J=6.8 Hz, 2H), 0.94 (t, J=7.3 Hz, 3H).

Step 2

Synthesis of [$^{11}$C]Flurbiprofen N-Propyl Ester (17)

[$^{11}$C]flurbiprofen n-propyl ester (17) was synthesized from the n-propyl 2-(2-fluorobiphenyl-4-yl)acetate (18) synthesized in the step 1 of Example 15 according to a similar procedure to Example 2. The reaction mixture thus obtained was separated by preparative HPLC (mobile phase; acetonitrile:water=75:25, column; COSMOSIL, 5C$_{18}$-MS-II, inner diameter 20 mm×length 250 mm, particle diameter 5 μm, flow rate; 10 mL/min, UV detector; 254 nm); as a result, [$^{11}$C]flurbiprofen n-propyl ester (17) was eluted at a retention time of 13 minutes as shown in FIG. 15.

A radioactivity was 1.4 GBq on completion of the reaction, and a specific radioactivity was 26 GBq/μmol. A total time for synthesis and separation of [$^{11}$C]flurbiprofen n-propyl ester (17), and preparation of an intravenous injection solution was about 34 minutes. An authentic sample of flurbiprofen n-propyl ester (J. Org. Chem. 1994, 59, 4410-4417) was mixed and a result of analytical HPLC showed a single peak, thereby determining identification of the [$^{11}$C]flurbiprofen n-propyl ester (17) (mobile phase; acetonitrile:water=70:30, column; COSMOSIL, 5C$_{18}$-AR-II, inner diameter 4.6 mm×length 100 mm, particle diameter 5 μm, flow rate; 1 mL/min, UV detector; 254 nm). As a result, a retention time was 5.7 minutes, and a purity was 99% or more.

Example 16

Synthesis of [$^{11}$C]Flurbiprofen 2-Propyl Ester (19)

[Chemical Formula 21]

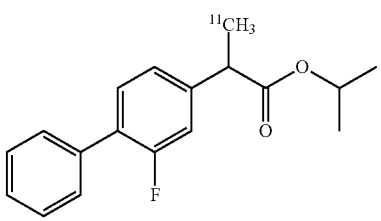

(19)

Step 1

Synthesis of 2-propyl (2-fluorobiphenyl-4-yl)acetate (20)

[Chemical Formula 22]

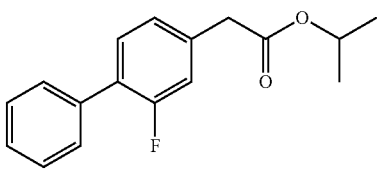

(20)

2-propyl (2-fluorobiphenyl-4-yl)acetate (20) was synthesized from 2-(2-fluorobiphenyl-4-yl)acetic acid and 2-propanol according to a similar procedure to step 1 of Example 15. The $^1$H NMR spectrum of this substance is shown below.

$^1$H NMR (400 MHz, CDCl$_3$)

δ: 7.55-7.53 (m, 2H), 7.46-7.36 (m, 4H), 7.14-7.10 (m, 2H), 3.91 (t, J=6.8 Hz, 1H), 3.66 (s, 2H), 0.92 (t, J=6.8 Hz, 6H).

Step 2

Synthesis of [$^{11}$C]flurbiprofen 2-propyl ester (19)

[$^{11}$C]flurbiprofen 2-propyl ester (19) was synthesized from the 2-propyl (2-fluorobiphenyl-4-yl)acetate (20) synthesized in the step 1 of Example 16 according to a similar procedure to Example 2. The reaction mixture thus obtained was separated by preparative HPLC (mobile phase; acetonitrile:water=75:25, column; COSMOSIL, $5C_{18}$-MS-II, inner diameter 20 mm×length 250 mm, particle diameter 5 μm, flow rate; 10 mL/min, UV detector; 254 nm); as a result, [$^{11}$C]flurbiroprofen 2-propyl ester (19) was eluted at a retention time of 11.4 minutes as shown in FIG. 16.

A radioactivity was 2.1 GBq on completion of the reaction, and a specific radioactivity was 19 GBq/μmol. A total time for synthesis and separation of [$^{11}$C]flurbiroprofen 2-propyl ester (19), and preparation of an intravenous injection solution was about 36 minutes. An authentic sample of flurbiroprofen 2-propyl ester (J. Controlled Rellease. 1999, 62, 223-229) was mixed and a result of analytical HPLC showed a single peak, thereby determining identification of the [$^{11}$C]flurbiroprofen 2-propyl ester (19) (mobile phase; acetonitrile:water=70:30, column; COSMOSIL, $5C_{18}$-AR-II, inner diameter 4.6 mm×length 100 mm, particle diameter 5 μm, flow rate; 1 mL/min, UV detector; 254 nm). As a result, a retention time was 5.7 minutes, and a purity was 99% or more.

Example 17

Synthesis of [$^{11}$C]flurbiprofen n-butyl ester (21)

[Chemical Formula 23]

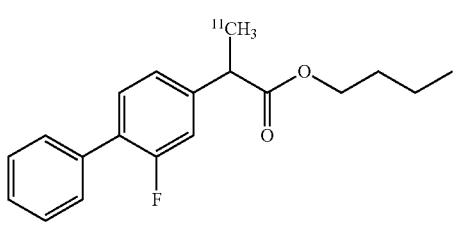

(21)

Step 1

Synthesis of n-butyl 2-(2-fluorobiphenyl-4-yl)acetate (22)

[Chemical Formula 24]

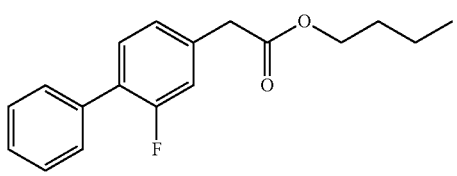

(22)

n-butyl 2-(2-fluorobiphenyl-4-yl)acetate (22) was synthesized from 2-(2-fluorobiphenyl-4-yl)acetic acid and n-butanol according to a similar procedure to the step 1 of Example 15. The $^1$H NMR spectrum of this substance is shown below.

$^1$H NMR (400 MHz, CDCl$_3$)

δ: 7.55-7.54 (m, 2H), 7.46-7.35 (m, 4H), 7.14-7.09 (m, 2H), 4.13 (t, J=6.8 Hz, 1H), 3.68 (s, 2H), 1.66-1.58 (m, 2H), 1.42-1.33 (m, 2H), 0.93 (t, J=7.3 Hz, 3H).

Step 2

Synthesis of [$^{11}$C]flurbiprofen n-butyl ester (21)

[$^{11}$C]flurbiprofen n-butyl ester (21) was synthesized from the n-butyl 2-(2-fluorobiphenyl-4-yl)acetate (22) synthesized in the step 1 of Example 17 according to a similar procedure to Example 2. The reaction mixture thus obtained was separated by preparative HPLC (mobile phase; acetonitrile:water=75:25, column; COSMOSIL, $5C_{18}$-MS-II, inner diameter 20 mm×length 250 mm, particle diameter 5 μm, flow rate; 10 mL/min, UV detector; 254 nm); as a result, [$^{11}$C]flurbiprofen n-butyl ester (21) was eluted at a retention time of 15.5 minutes as shown in FIG. 17.

A radioactivity was 1.5 GBq on completion of the reaction, and a specific radioactivity was 16 GBq/μmol. A total time for synthesis and separation of [$^{11}$C]flurbiprofen n-butyl ester (21), and preparation of an intravenous injection solution was about 39 minutes. An authentic sample of flurbiprofen n-butyl ester (JP57091913 A) was mixed and a result of analytical HPLC showed a single peak, thereby determining identification of the [$^{11}$C]flurbiprofen n-butyl ester (21) (mobile phase; acetonitrile:water=70:30, column; COSMOSIL, $5C_{18}$-AR-II, inner diameter 4.6 mm×length 100 mm, particle diameter 5 μm, flow rate; 1 mL/min, UV detector; 254 nm). As a result, a retention time was 5.4 minutes, and a purity was 99% or more.

Example 18

Synthesis of [$^{11}$C]flurbiprofen 2-methylpropyl ester (23)

[Chemical Formula 25]

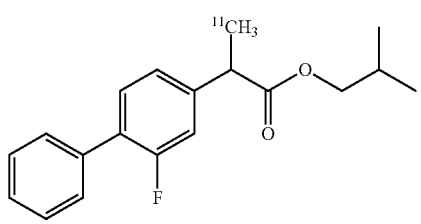

(23)

Step 1

Synthesis of 2-methylpropyl 2-(2-fluorobiphenyl-4-yl)acetate (24)

[Chemical Formula 26]

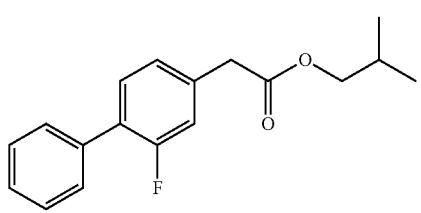

(24)

2-methylpropyl 2-(2-fluorobiphenyl-4-yl)acetate (24) was synthesized from 2-(2-fluorobiphenyl-4-yl)acetic acid and 2-methyl propanol according to a similar procedure to step 1 of Example 15. The $^1$H NMR spectrum of this substance is shown below.

$^1$H NMR (400 MHz, CDCl$_3$)

δ: 7.55-7.54 (m, 2H), 7.46-7.35 (m, 4H), 7.14-7.09 (m, 2H), 4.13 (t, J=6.8 Hz, 1H), 3.68 (s, 2H), 0.93 (t, J=7.3 Hz, 3H).

Step 2

Synthesis of [$^{11}$C]flurbiprofen 2-methylpropyl ester (23)

[$^{11}$C]flurbiprofen 2-methylpropyl ester (23) was synthesized from the 2-methylpropyl 2-(2-fluorobiphenyl-4-yl)acetate (24) synthesized in the step 1 of Example 18 according to a similar procedure to Example 2. The reaction mixture thus obtained was separated by preparative HPLC (mobile phase; acetonitrile:water=75:25, column; COSMOSIL, 5C$_{18}$-MS-II, inner diameter 20 mm×length 250 mm, particle diameter 5 μm, flow rate; 10 mL/min, UV detector; 254 nm); as a result, [$^{11}$C]flurbiprofen 2-methylpropyl ester (23) was eluted at a retention time of 15.5 minutes as shown in FIG. 18.

A radioactivity was 1.5 GBq on completion of the reaction, and a specific radioactivity was 26 GBq/μmol. A total time for synthesis and separation of [$^{11}$C]flurbiprofen 2-methylpropyl ester (23), and preparation of an intravenous injection solution was about 39 minutes. An authentic sample of flurbiprofen 2-methylpropyl ester (Ind. J. Chem. Section B: Organic Chemistry Including Medicinal Chemistry, 2007, 46B, 1164-1168) was mixed and a result of analytical HPLC showed a single peak, thereby determining identification of the [$^{11}$C] flurbiprofen 2-methylpropyl ester (23) (mobile phase; acetonitrile:water=70:30, column; COSMOSIL, 5C$_{18}$-AR-II, inner diameter 4.6 mm×length 100 mm, particle diameter 5 μm, flow rate; 1 mL/min, UV detector; 254 nm). As a result, a retention time was 5.4 minutes, and a purity was 99% or more.

Example 19

Synthesis of [$^{11}$C]Methyl Flurbiprofen (25)

[Chemical Formula 27]

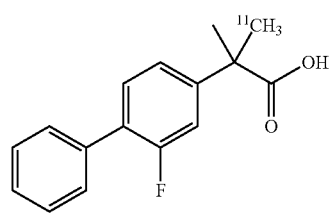

(25)

A flurbiprofen methyl ester was used as a starting material, and [$^{11}$C]methyl flurbiprofen (25) was synthesized according to a method similar to the method of Example 1. The reaction mixture thus obtained was separated by preparative HPLC (mobile phase; acetonitrile:10 mM sodium phosphate buffer (pH 7.4)=80:20, column; COSMOSIL, 5C$_{18}$-MS-II, inner diameter 20 mm×length 250 mm, particle diameter 5 μm, flow rate; 10 mL/min, UV detector; 254 nm); as a result, [$^{11}$C]methylflurbiprofen (25) was eluted at a retention time of 14 minutes as shown in FIG. 19.

A radioactivity was 3.68 GBq on completion of the reaction, and a specific radioactivity was 42 GBq/μmol. A total time for synthesis and separation of [$^{11}$C]methylflurbiprofen (25), and preparation of an intravenous injection solution was about 32 minutes. An authentic sample of methylflurbiprofen (Bioorg. Med. Chem. Lett. 2006, 16, 2219-222) was mixed and a result of analytical HPLC showed a single peak, thereby determining identification of the [$^{11}$C]methylflurbiprofen (25) (mobile phase; acetonitrile:0.1% phosphoric acid=50:50, column; COSMOSIL, 5C$_{18}$-AR-II, inner diameter 4.6 mm×length 100 mm, particle diameter 5 μm, flow rate; 1 mL/min, UV detector; 254 nm). As a result, a retention time was 7.6 minutes, and a purity was 99% or more.

Example 20

Synthesis of [$^{11}$C]Methyl Flurbiprofen Methyl Ester (26)

[Chemical Formula 28]

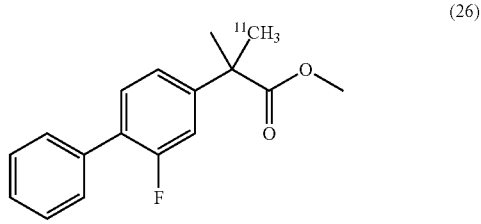

(26)

Flurbiprofen methyl ester was used as a starting material, and [$^{11}$C]methyl flurbiprofen methyl ester (26) was synthesized according to a method similar to the method of Example 2. The reaction mixture thus obtained was separated by preparative HPLC (mobile phase; acetonitrile:water=80:20, column; COSMOSIL, 5C$_{18}$-MS-II, inner diameter 20 mm×length 250 mm, particle diameter 5 μm, flow rate; 10 mL/min, UV detector; 254 nm); as a result, [$^{11}$C]methylflurbiprofen methyl ester (26) was eluted at a retention time of 17 minutes as shown in FIG. 20.

A radioactivity was 2.32 GBq on completion of the reaction, and a specific radioactivity was 37 GBq/μmol. A total time for synthesis and separation of [$^{11}$C]methyl flurbiprofen methyl ester (26), and preparation of an intravenous injection solution was about 32 minutes. An authentic sample of methyl flurbiprofen methyl ester (Bioorg. Med. Chem. Lett. 2006, 16, 2219-222) was mixed and a result of analytical HPLC showed a single peak, thereby determining identification of the [$^{11}$C]methyl flurbiprofen methyl ester (26) (mobile phase; acetonitrile:water=65:35, column; COSMOSIL, 5C$_{18}$-AR-II, inner diameter 4.6 mm×length 100 mm, particle diameter 5 μm, flow rate; 1 mL/min, UV detector; 254 nm). As a result, a retention time was 6.9 minutes, and a purity was 99% or more.

Example 21

Synthesis of (R)—[$^{11}$C]Flurbiprofen Methyl Ester (27R) and (S)—[$^{11}$C]Flurbiprofen Methyl Ester (27S)

[Chemical Formula 29]

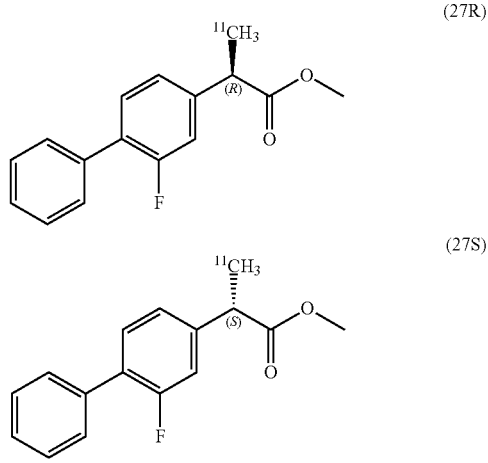

Methyl 2-(2-fluorobiphenyl-4-yl)acetate was used as a starting material, and (R)—[$^{11}$C]flurbiprofen methyl ester (27R) and (S)—[$^{11}$C]flurbiprofen methyl ester (27S) were synthesized according to a method similar to the method of Example 2.

Identification of (R)—[$^{11}$C]Flurbiprofen Methyl Ester (27R)

The reaction mixture obtained in the above synthesis reaction was separated by preparative HPLC (mobile phase; methanol:water=90:10, column; CHIRALCEL OJ-RH, inner diameter 20 mm×length 150 mm, particle diameter 5 μm, flow rate; 10 mL/min, UV detector; 254 nm); as a result, (R)—[$^{11}$C]flurbiprofen methyl ester (27R) was eluted at a retention time of 17 minutes as shown in FIG. 21. An authentic sample of (R)-flurbiprofen methyl ester was mixed and a result of analytical HPLC showed a single peak, thereby determining identification of the (R)—[$^{11}$C]methyl ester (27R).

Identification of (S)—[$^{11}$C]Flurbiprofen Methyl Ester (27S)

On the other hand, the reaction mixture obtained in the above synthesis reaction was separated by preparative HPLC (mobile phase; methanol:water=90:10, column; CHIRALCEL OJ-RH, inner diameter 20 mm×length 150 mm, particle diameter 5 μm, flow rate; 10 mL/min, UV detector; 254 nm); as a result, (S)—[$^{11}$C]flurbiprofen methyl ester (27S) was eluted at a retention time of 22 minutes as shown in FIG. 21. An authentic sample of (S)-flurbiprofen methyl ester was mixed and a result of analytical HPLC showed a single peak, thereby determining identification of the (S)—[$^{11}$C]flurbiprofen methyl ester (27S).

<PET Imaging Using Brain Inflammation Model Rat>

PET was performed using a brain inflammation model rat for the [$^{11}$C]ketoprofen methyl ester (8) synthesized in Example 6. In the experiment, a trace amount, 0.5 μg, of lipopolysaccharide (LPS) that is a constituent of a gram-negative bacteria cell wall outer membrane was injected into the left striatum of a rat, thereby inducing brain inflammation (Hunter R L, Dragicevic N, Seifert K, Choi D Y, Liu M, Kim H C, Cass W A, Sullivan P G, Bing G. Inflammation induces mitochondrial dysfunction and dopaminergic neurodegeneration in the nigrostriatal system. J. Neurochem. 2007100: 5:1375-86.). The [$^{11}$C]ketoprofen methyl ester (8) was administered to a rat after 1 day from injection of LPS through a caudal vein, PET was performed for 45 minutes using a PET apparatus for small animals (manufactured by microPET, SIMENS). The injection solution of the [$^{11}$C]ketoprofen methyl ester (radioactivity 72 to 74 MBq) was prepared by diluting with saline to 1.0 CC volume. In order to further study an effect of inhibiting bonds by a non-RI labeled body, an injection solution added with 10 mg/kg of ketoprofen methyl ester (final concentration of a solvent was 5% DMSO, 5% tween20) was prepared. On completion of PET imaging, a rat brain section was prepared and an Ex vivo autoradiography (ARG) experiment was performed. In the experiment, the rat was perfused with saline, and a section prepared with 2 mm thickness, which was obtained from the brain taken out from the rat, was exposed on an imaging plate BAS SR-2040 (manufactured by Fujifilm Corporation) for 1 hour to read using a fluoroimage analyzer (FLA7000). In order to identify an expression site of cyclooxygenase-2, chemical staining of an immune tissue in a brain section was performed using a specific antibody. That is, 20 μm of a frozen section prepared from the brain section used in the autoradiography mentioned above and pasted on a slide glass was incubated with anti-cyclooxygenase-2 (rabbit IgG, polyclonal antibody, manufactured by Cayman) diluted to PBS-T at a concentration of 200 times as a primary antibody at 4° C. overnight. Next, the brain section was reacted with a biotin labeled anti-rabbit IgG antibody (manufactured by VECTOR) diluted to PBS-T at a concentration of 200 times at room temperature for 1 hour to bond with an avidin-biotin labeled peroxydase complex (VECTASTAIN Elite ABC Kit, manufactured by VECTOR). In the method of dye, a DAB method of reacting with diaminobenzine was used.

<Results>

An addition average of PET images in 45 minutes after administration of the [$^{11}$C]ketoprofen methyl ester, and an amount of radioactivity were shown in FIG. 22a, and radioactivity over elapsed times in each brain site at the time was shown in FIG. 22b. FIG. 22a indicates that the [$^{11}$C]ketoprofen methyl ester (8) passed through the blood-brain barrier and accumulated in an inflammation region around the LPS injected site in the left side of the brain. This accumulation was significantly reduced by administration of 10 mg/kg of non-RI labeled ketoprofen methyl ester, and thus, accumulation in an inflammation region of [$^{11}$C]ketoprofen methyl ester was found to be specific. In addition, it was found as shown in FIG. 23 that the [$^{11}$C]ketoprofen methyl ester was accumulated specifically in an inflammation site also in the autoradiography (ARG) experiment using a rat brain section, similar to the time of taking PET images. Furthermore, as a result of performing immune tissue chemical staining, an accumulated site of the [$^{11}$C]ketoprofen methyl ester was correspond with a positive site of immunostaining of cyclooxygenase-2, as shown in FIG. 24. These facts demonstrated that use of the [¹¹C]ketoprofen methyl ester (8) in Example 6 enables imaging of cyclooxygenase-2 in the brain as the first case in the world.

<PET Imaging of Alzheimer Disease Model Animal>

PET images were taken using an Alzheimer disease model mouse for the [¹¹C]ketoprofen methyl ester (21) synthesized in Example 6. For the Alzheimer disease model mouse, a transgenic mouse (APP-Tg) excessively expressing amyloid precursor protein (APP) in familial Alzheimer disease was purchased from Taconic Farms, Inc. USA to be used. In 24 months old when accumulation of amyloid β protein was confirmed as pathological change of Alzheimer disease, the [¹¹C]ketoprofen methyl ester (21) was administered through a caudal vein, and PET images were taken for 30 minutes using a PET apparatus for small animals (microPET, manufactured by SIMENS). The injection solution of the [¹¹C] ketoprofen methyl ester (21) (radioactivity 45 to 60 MBq) was prepared by diluting with saline to 1.0 CC volume. SUV (Standard Uptake Value)=tissue radioactivity in region of interest (MBq/g)÷[administration amount (MBq)/body weight (g)] was used as the index of an accumulation level, to compare with a brain of a wild type mouse that is a normal mouse in terms of an accumulation amount into the APP-Tg mouse brain.

<Results>

An addition average of PET images in 25 minutes after 5 minutes from administration of the [¹¹C]ketoprofen methyl ester (21), and a quantitative value of an accumulation amount (SUV) were shown in FIG. 25. It was shown that the [¹¹C]ketoprofen methyl ester (21) was highly accumulated in the APP-Tg mouse brain as compared with the wild type mouse brain. It was also shown from the quantitative value that a site showing high accumulation of [¹¹C]ketoprofen methyl ester is corresponded with a site that was reported of accumulation of amyloid β that is a main constituent of senile plaque in the APP-Tg mouse brain (Am J Pathol. 1998; 152 (1): 307-17.). These facts demonstrated that use of the [¹¹C] ketoprofen methyl ester (21) enables imaging of brain inflammation involved in neurodegeneration in Alzheimer disease.

The present invention is not necessarily limited to the exemplary embodiment and examples described so far. The present invention includes various modified embodiments as far as they stay within the Scope of Claims and can be easily assumed by the ordinarily skilled in the art.

BRIEF DESCRIPTION OF THE DRAWINGS

FIG. 22(a) shows an addition average of PET images in 45 minutes after administration of the [¹¹C]ketoprofen methyl ester (described as ¹¹C-KTP-Me) (8) synthesized in Example 6, and a ratio of an amount of radioactivity in each brain site using cerebellum as a reference region. Note that the PET images are overlapped with the standard MRI brain image. FIG. 22(b) shows an elapsed time of radioactivity. (SUV: tissue radioactivity in region of interest (MBq/g)÷[administration amount (MBq)/body weight (g)]).

INDUSTRIAL APPLICABILITY

Figure 1:
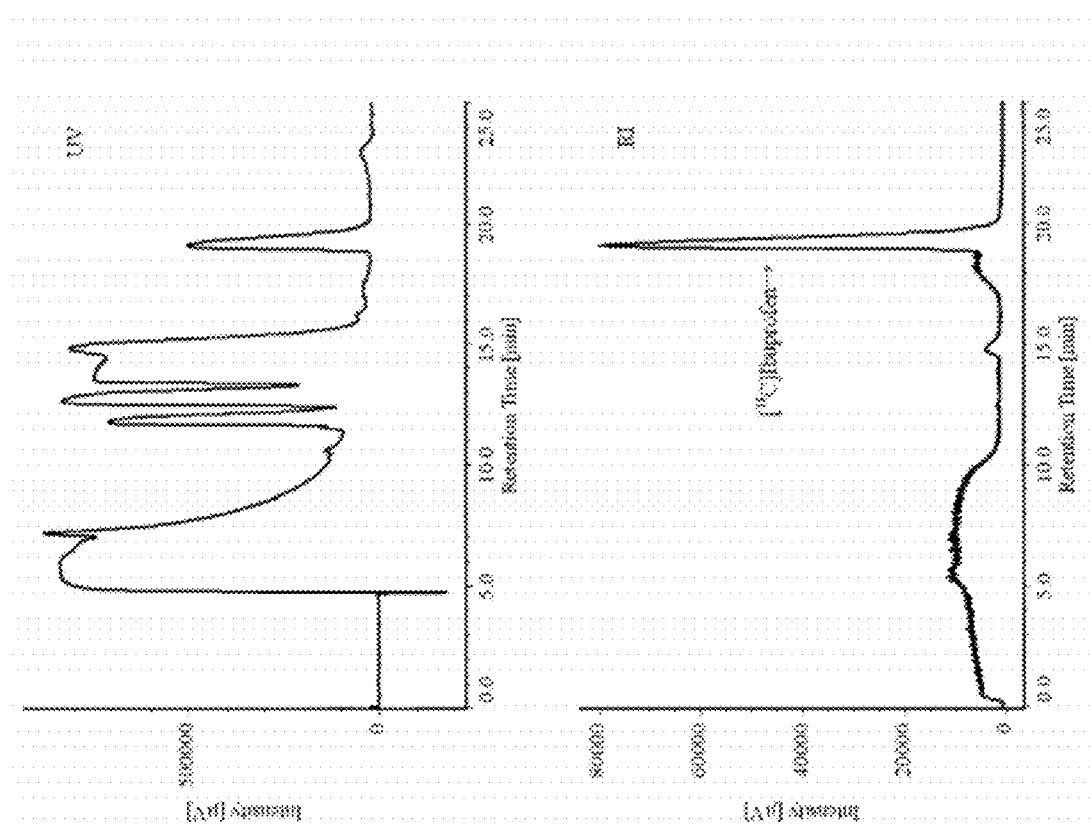
FIG. 1 is a HPLC chart of the reaction mixture in Example 1, and the arrow shows a peak of [¹¹C]ibuprofen.
Figure 2:
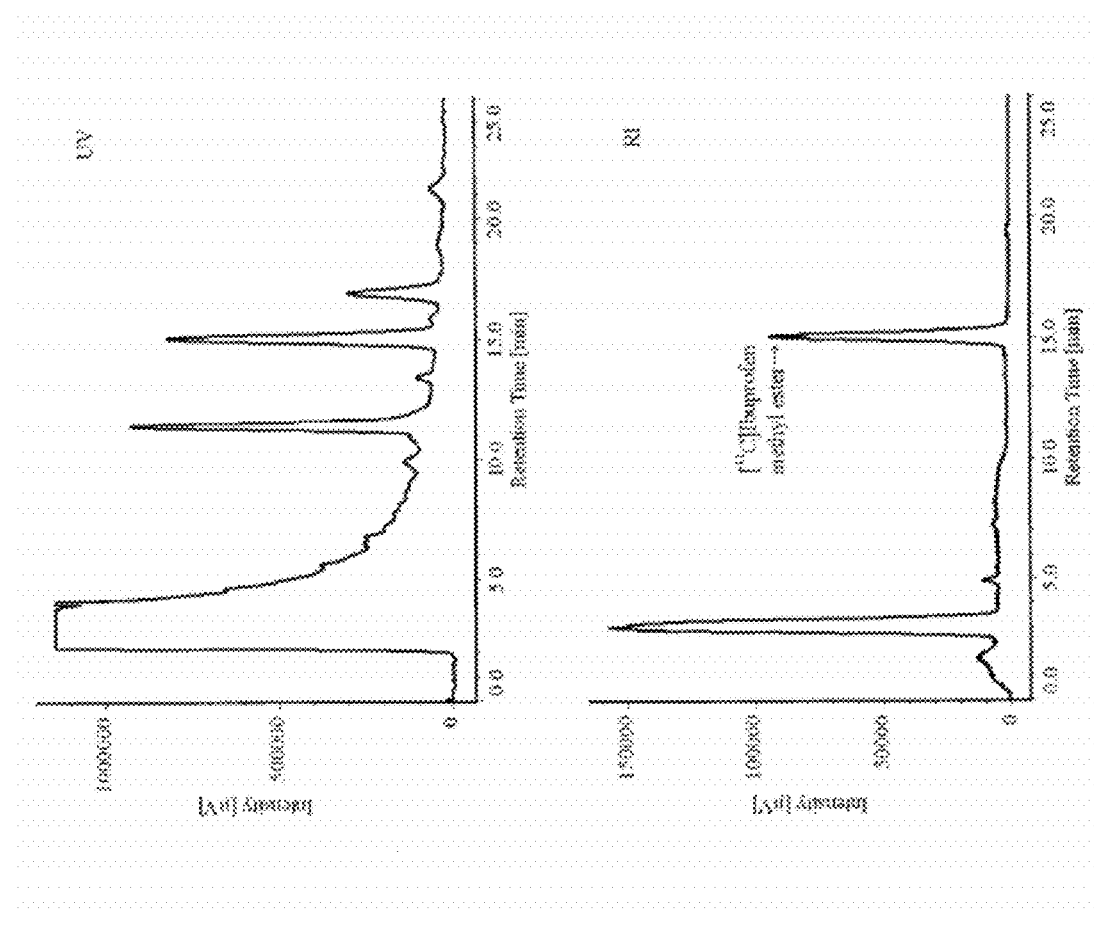
FIG. 2 is a HPLC chart of the reaction mixture in Example 2, and the arrow shows a peak of [¹¹C]ibuprofen methyl ester.
Figure 3:
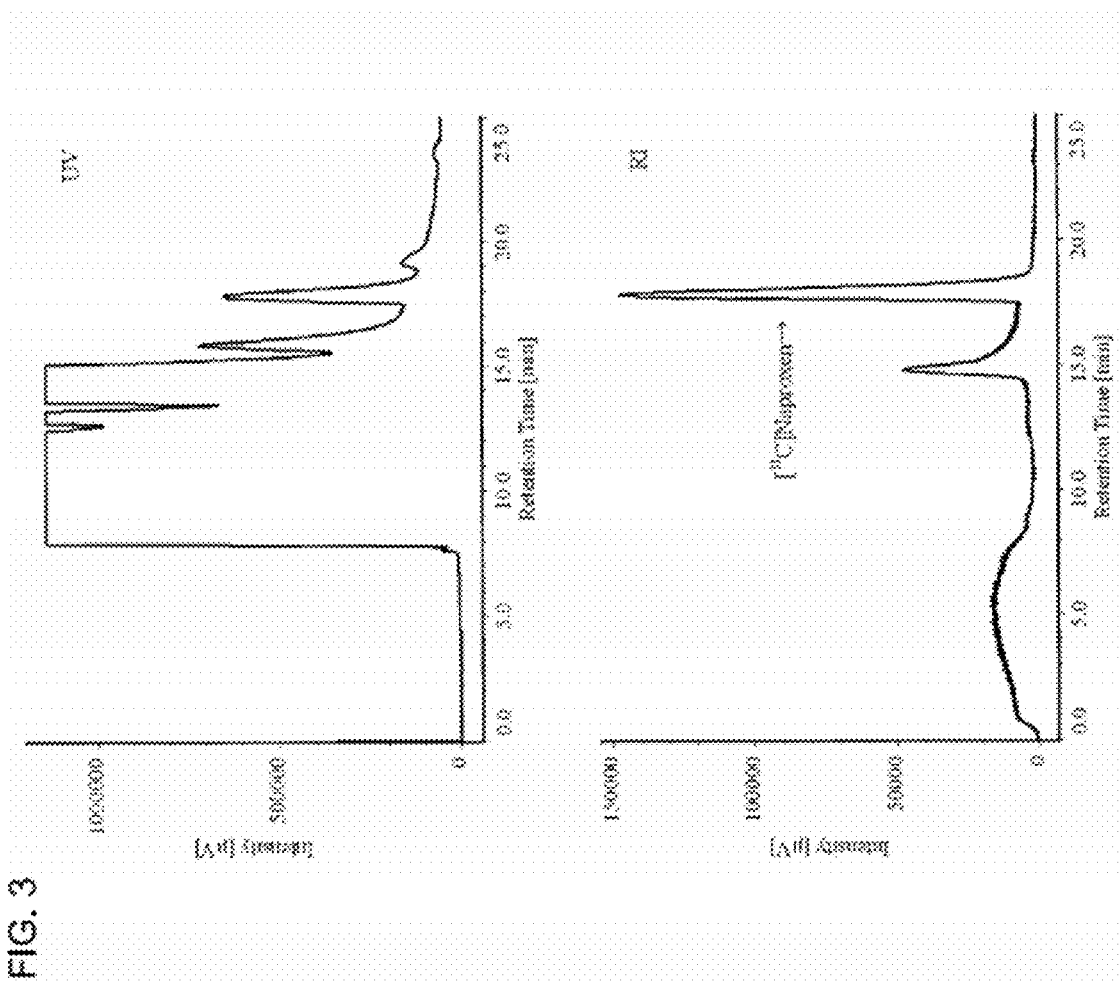
FIG. 3 is a HPLC chart of the reaction mixture in Example 3, and the arrow shows a peak of [¹¹C]naproxen.
Figure 4:
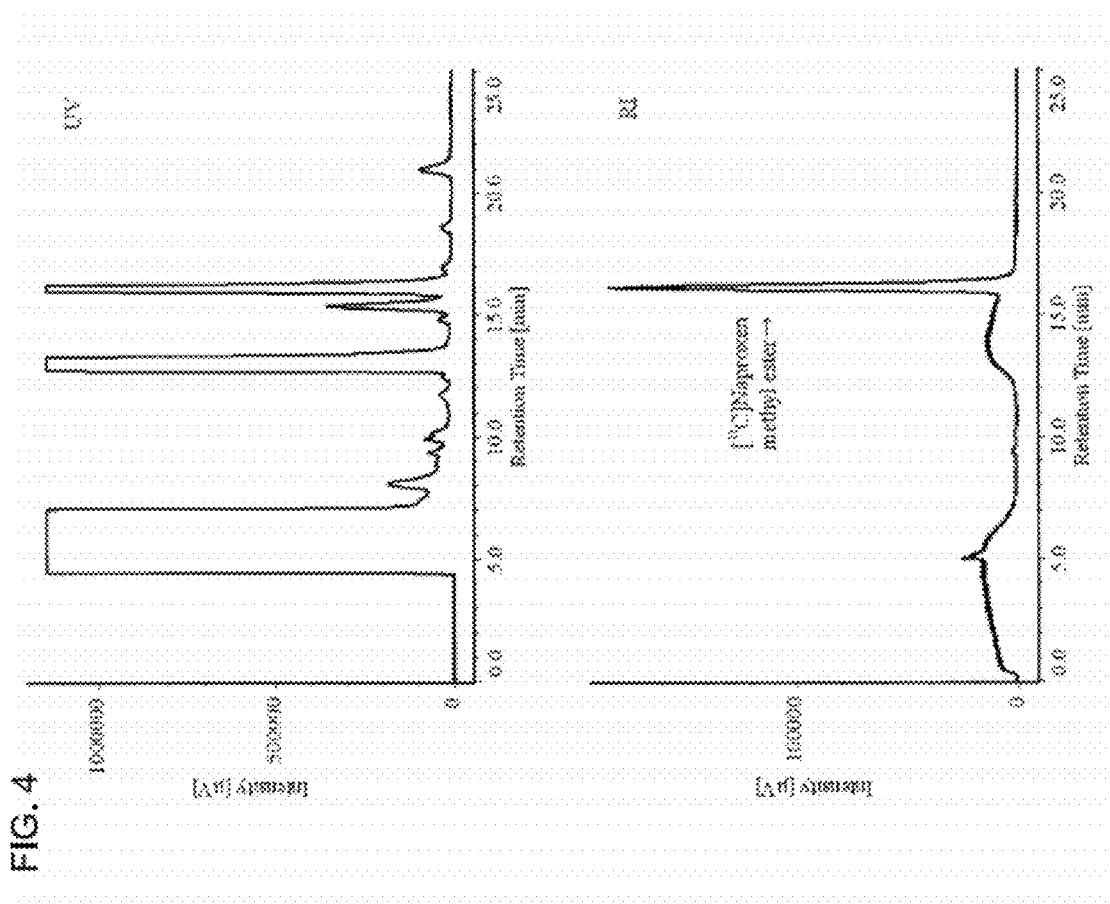
FIG. 4 is a HPLC chart of the reaction mixture in Example 4, and the arrow shows a peak of [¹¹C]naproxen methyl ester.
Figure 5:
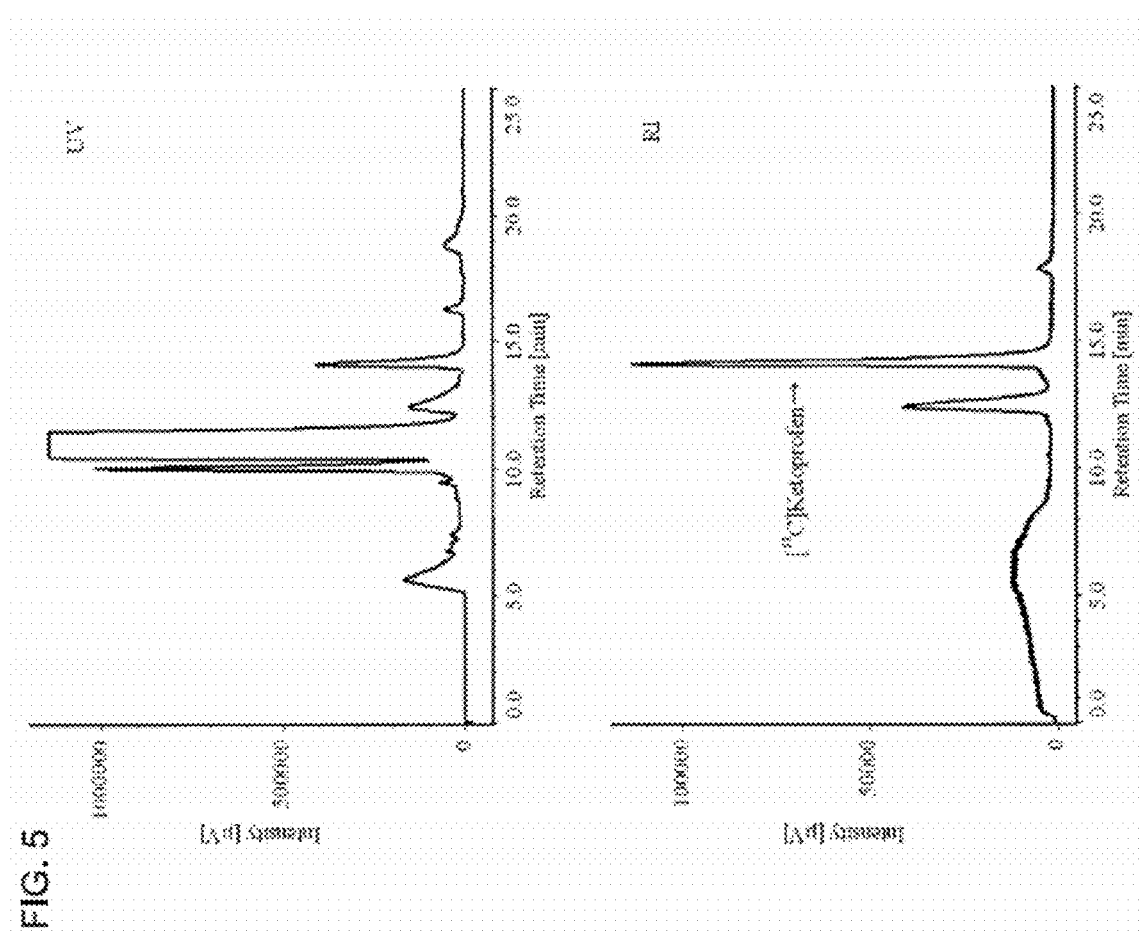
FIG. 5 is a HPLC chart of the reaction mixture in Example 5, and the arrow shows a peak of [¹¹C]ketoprofen.
Figure 6:
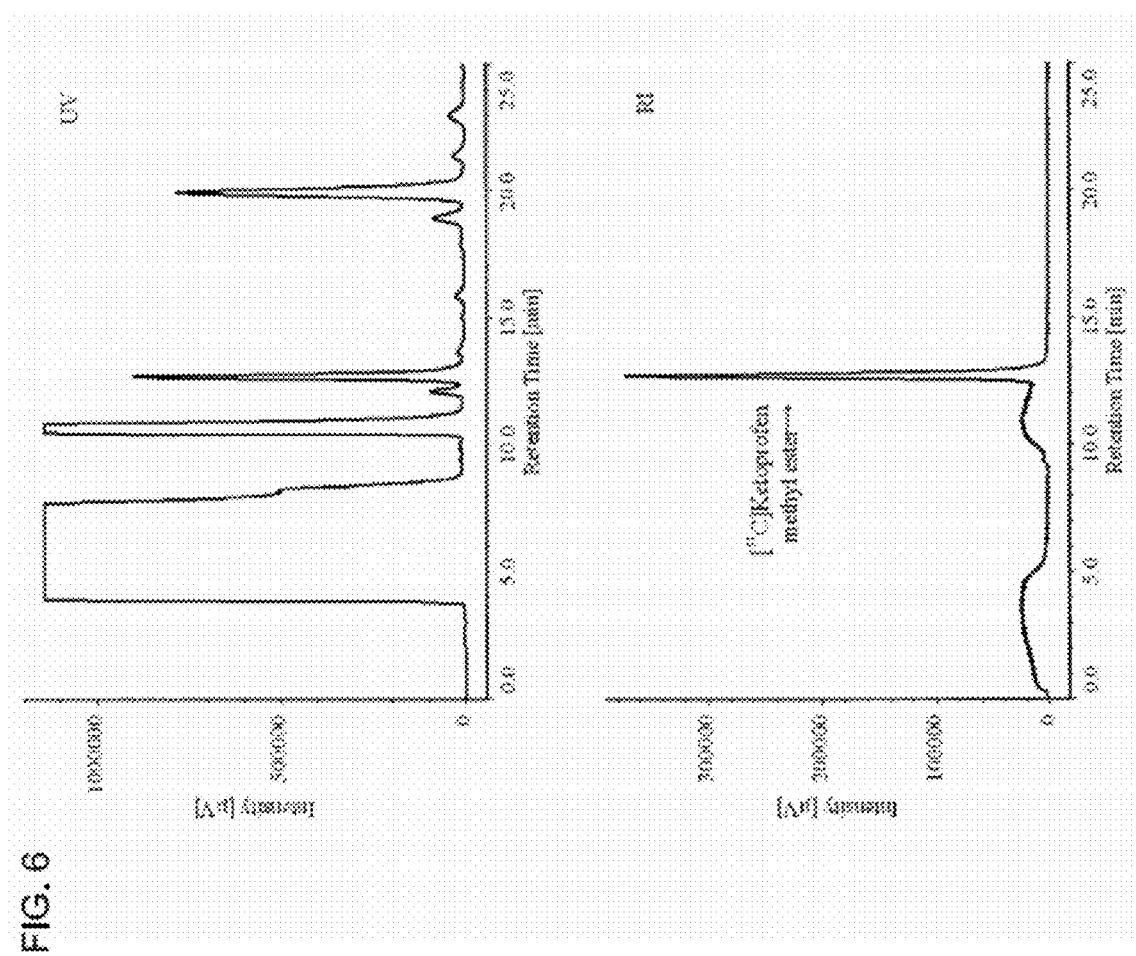
FIG. 6 is a HPLC chart of the reaction mixture in Example 6, and the arrow shows a peak of [¹¹C]ketoprofen methyl ester.
Figure 7:
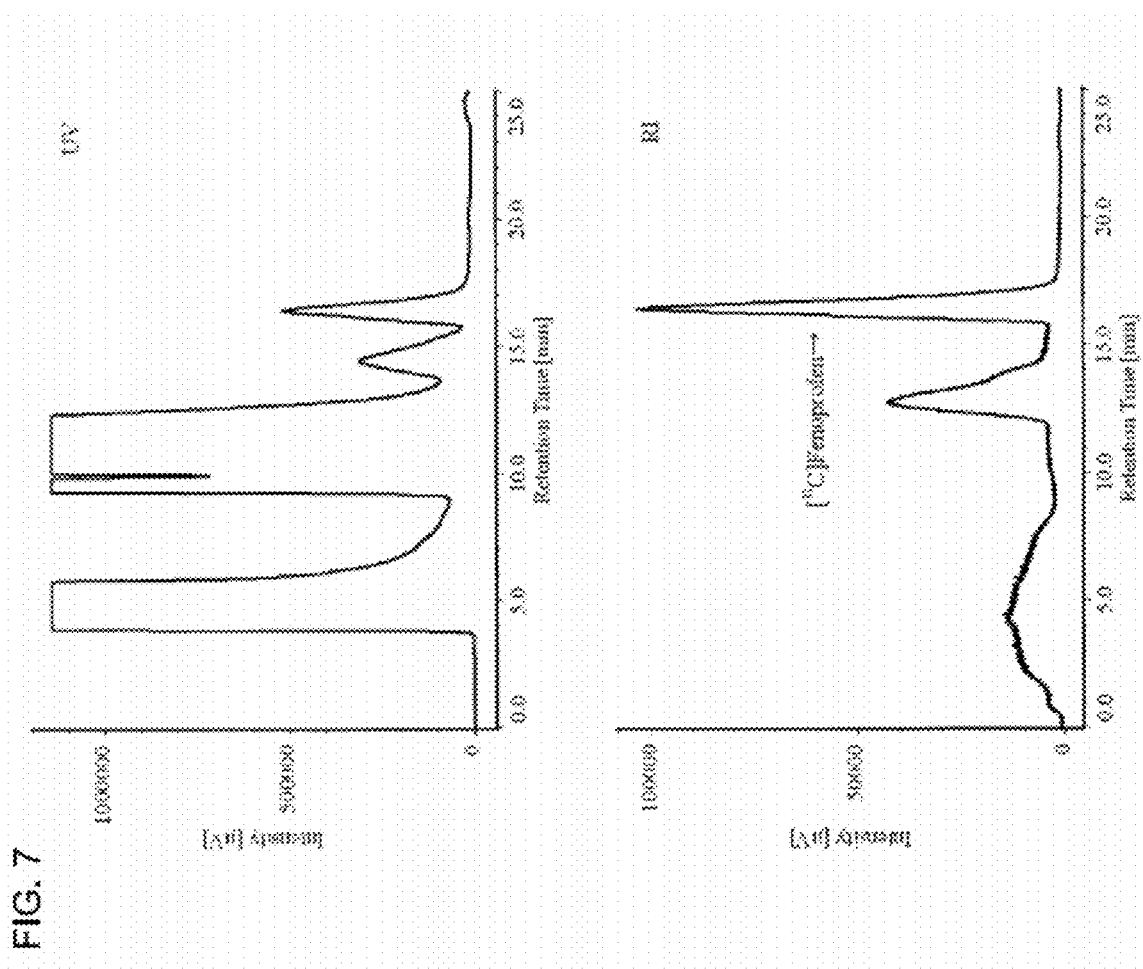
FIG. 7 is a HPLC chart of the reaction mixture in Example 7, and the arrow shows a peak of [¹¹C]fenoprofen.
Figure 8:
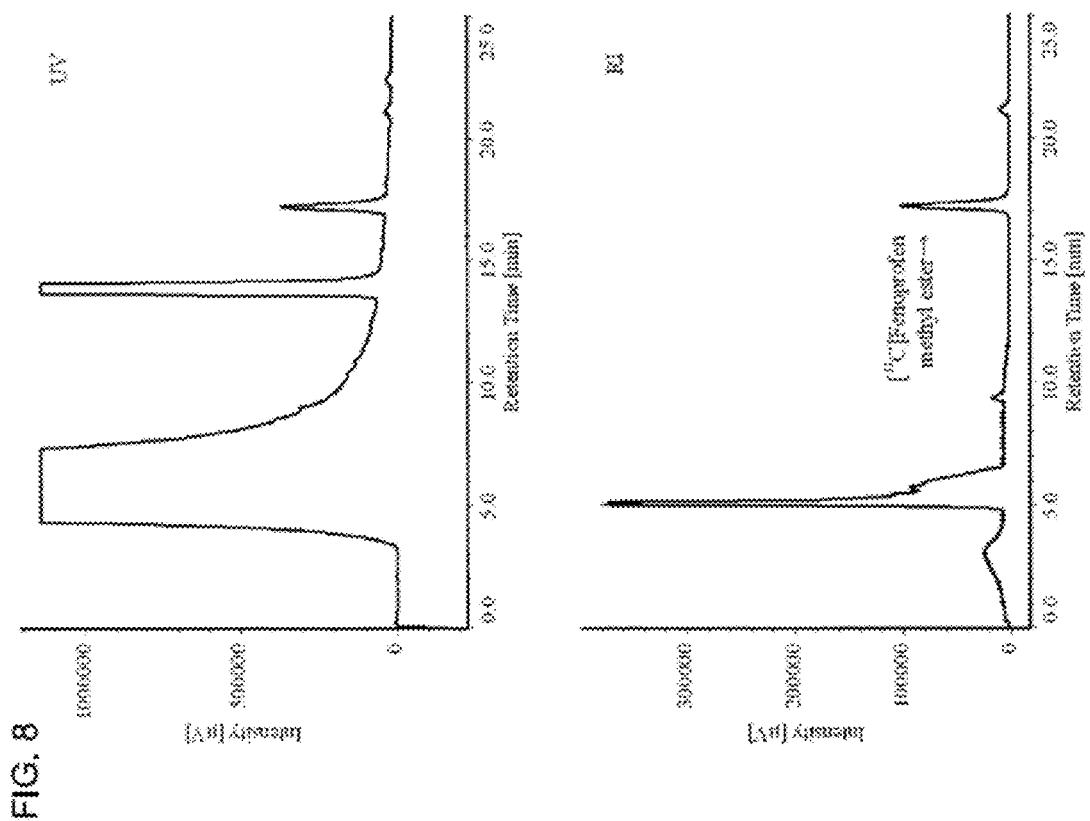
FIG. 8 is a HPLC chart of the reaction mixture in Example 8, and the arrow shows a peak of [¹¹C]fenoprofen methyl ester.
Figure 9:
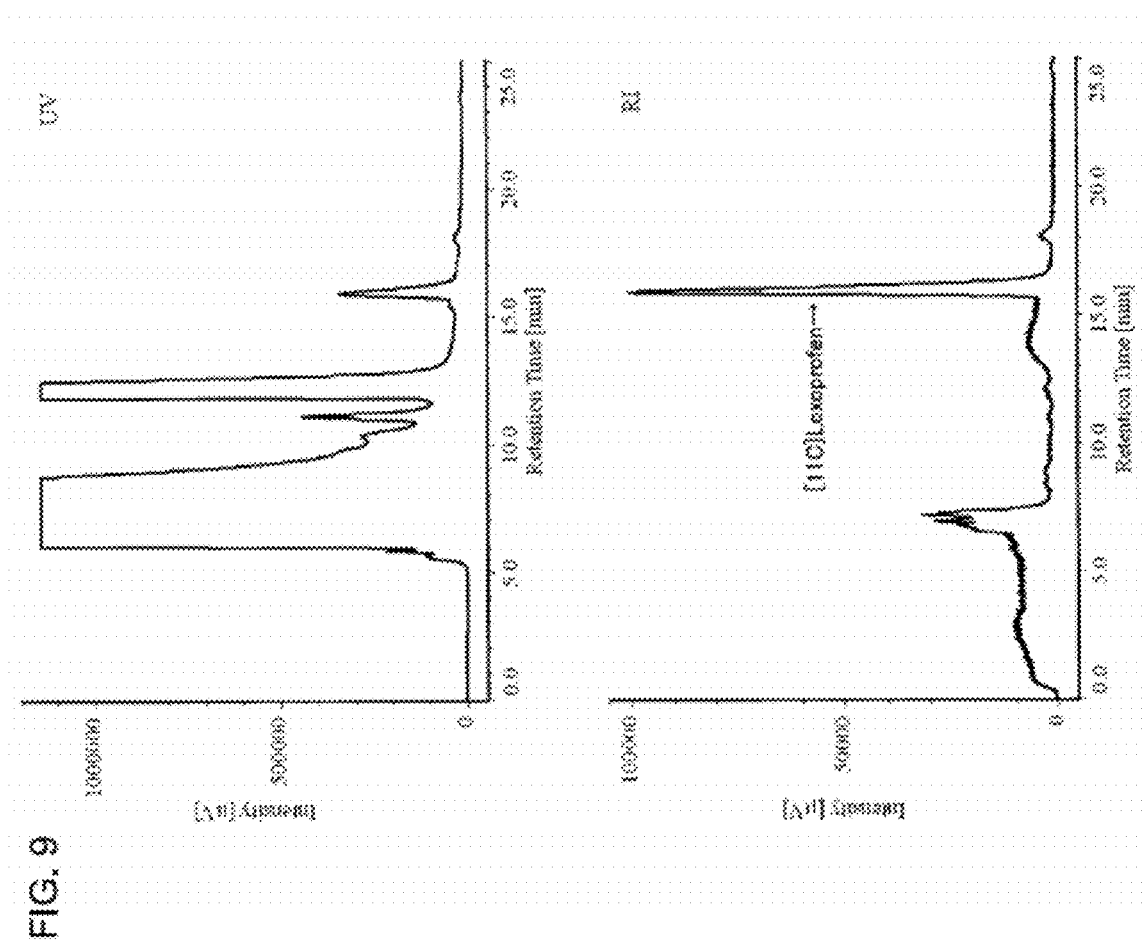
FIG. 9 is a HPLC chart of the reaction mixture in Example 9, and the arrow shows a peak of [¹¹C]loxoprofen (11).
Figure 10:
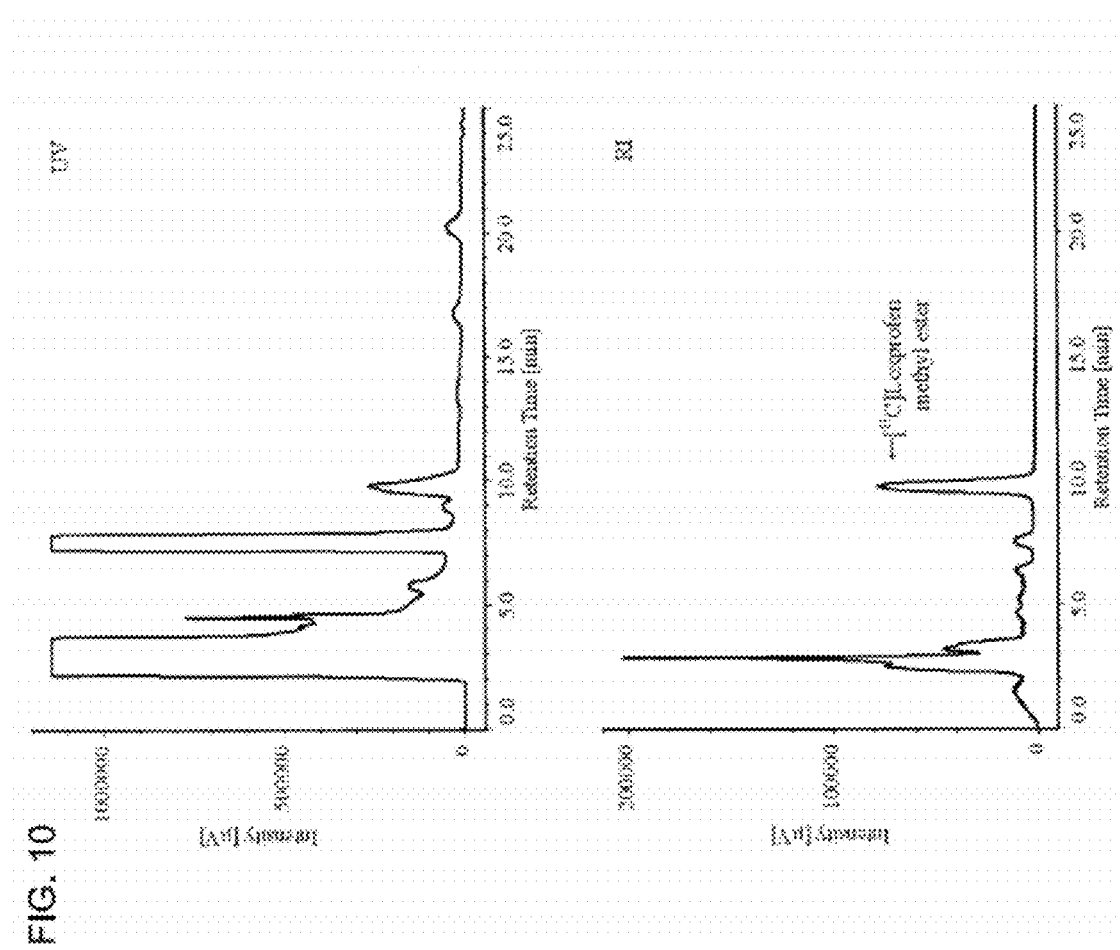
FIG. 10 is a HPLC chart of the reaction mixture in Example 10, and the arrow shows a peak of [¹¹C]loxoprofen methyl ester (12).
Figure 11:
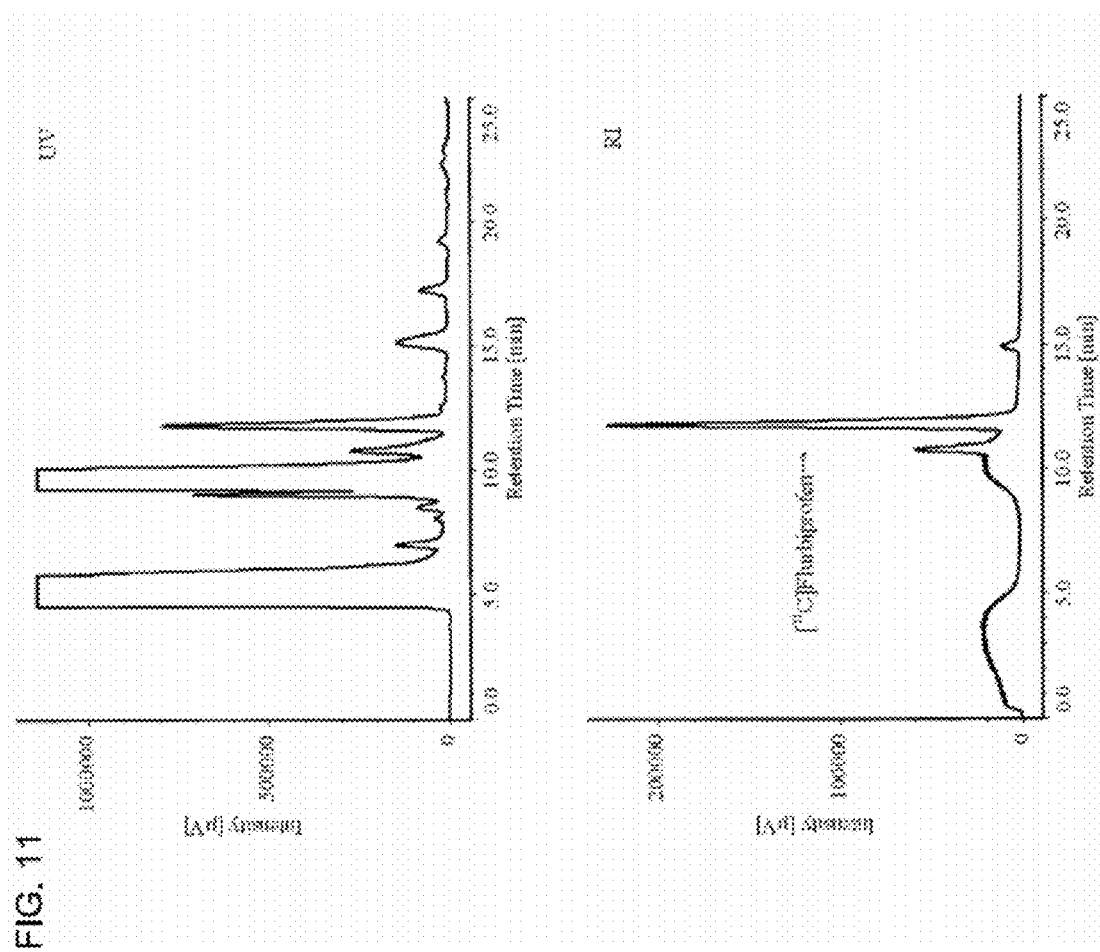
FIG. 11 is a HPLC chart of the reaction mixture in Example 11, and the arrow shows a peak of [¹¹C]flurbiprofen
Figure 12:
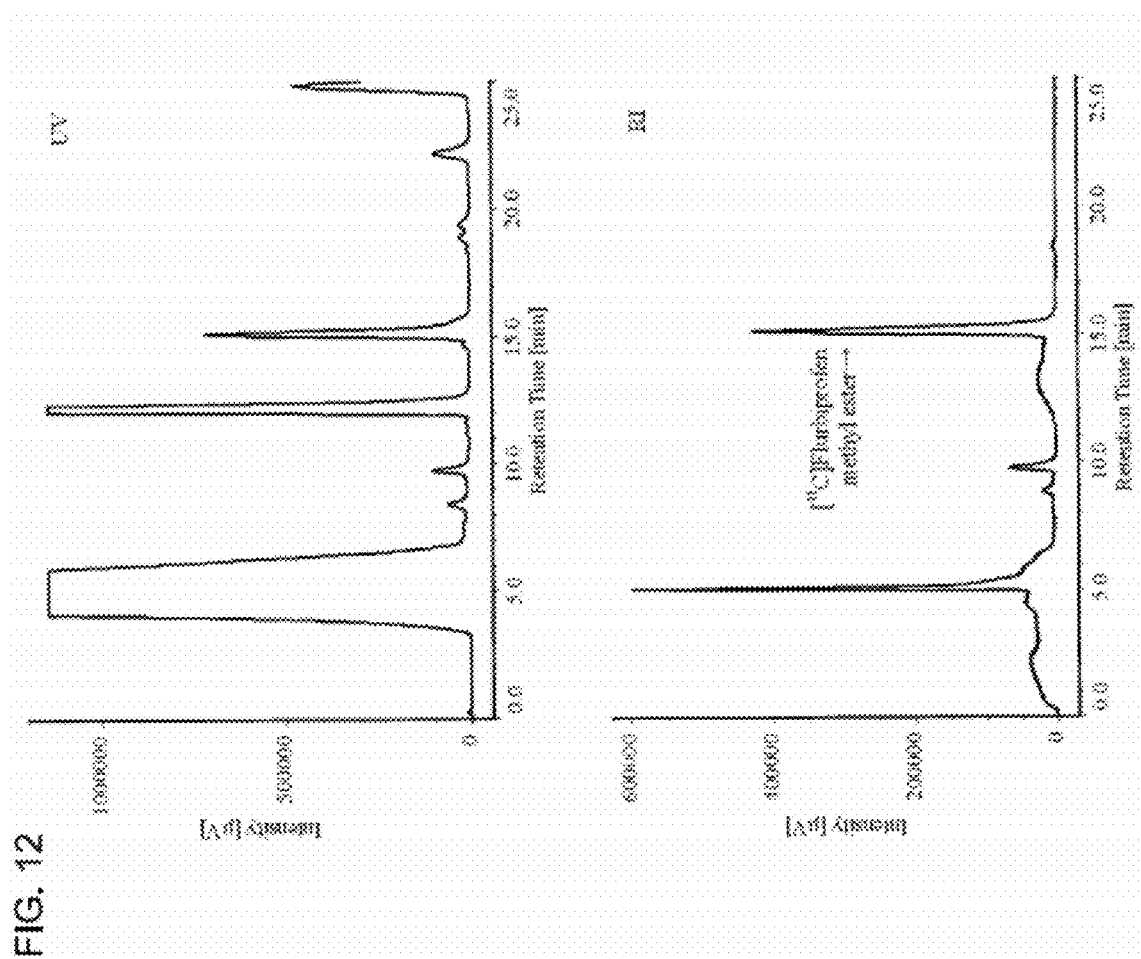
FIG. 12 is a HPLC chart of the reaction mixture in Example 12, and the arrow shows a peak of [¹¹C]flurbiprofen methyl ester.
Figure 13:
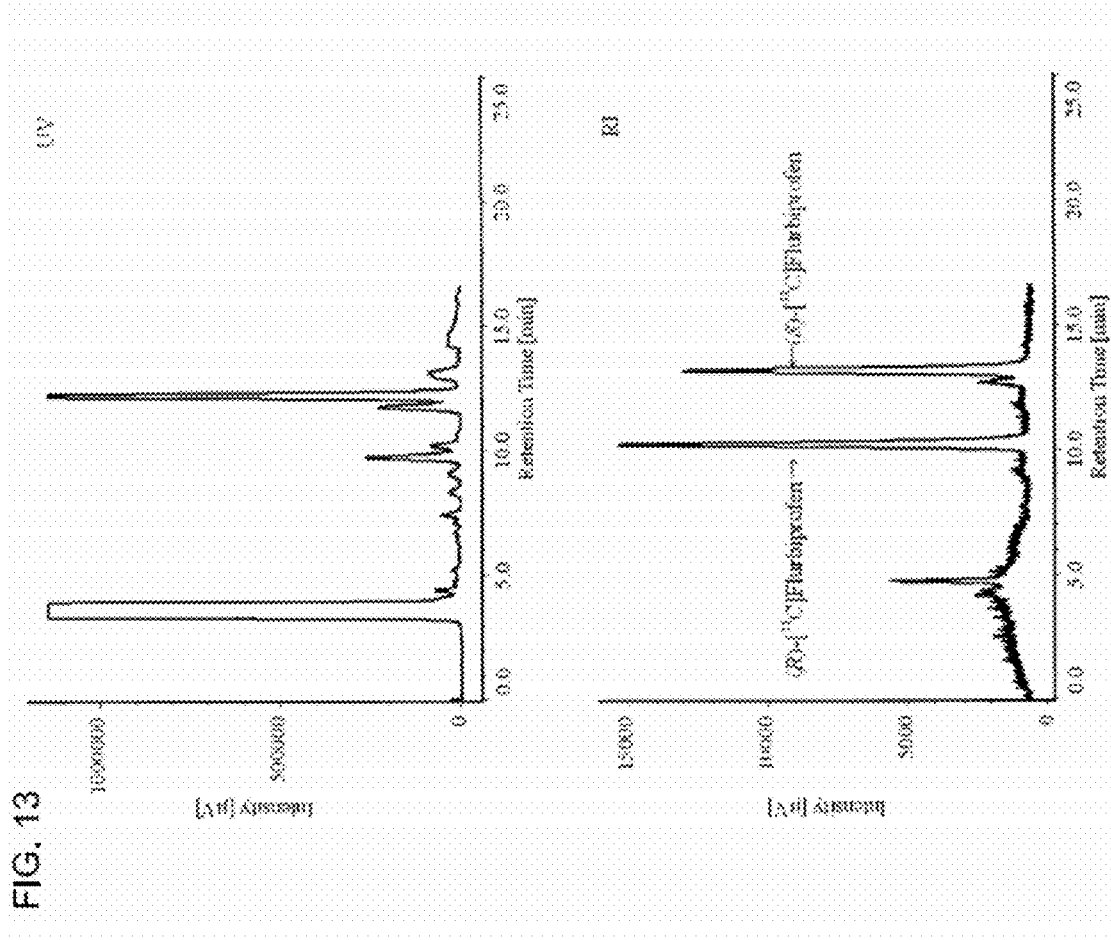
FIG. 13 is a HPLC chart of the reaction mixture in Example 13, and arrows show peaks of (R)—[¹¹C]flurbiprofen and (S)—[¹¹C]flurbiprofen.
Figure 14:
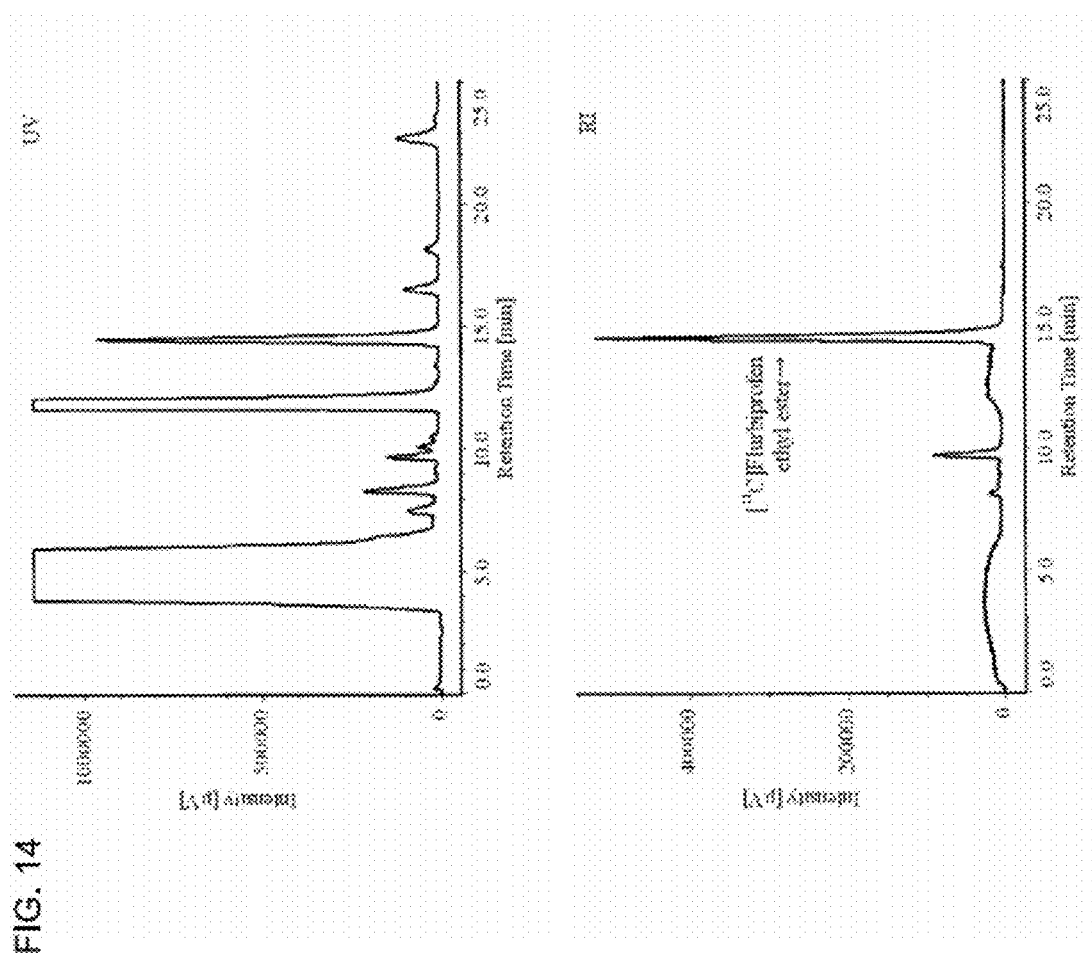
FIG. 14 is a HPLC chart of the reaction mixture in Example 14, and the arrow shows a peak of [¹¹C]flurbiprofen ethyl ester.
Figure 15:
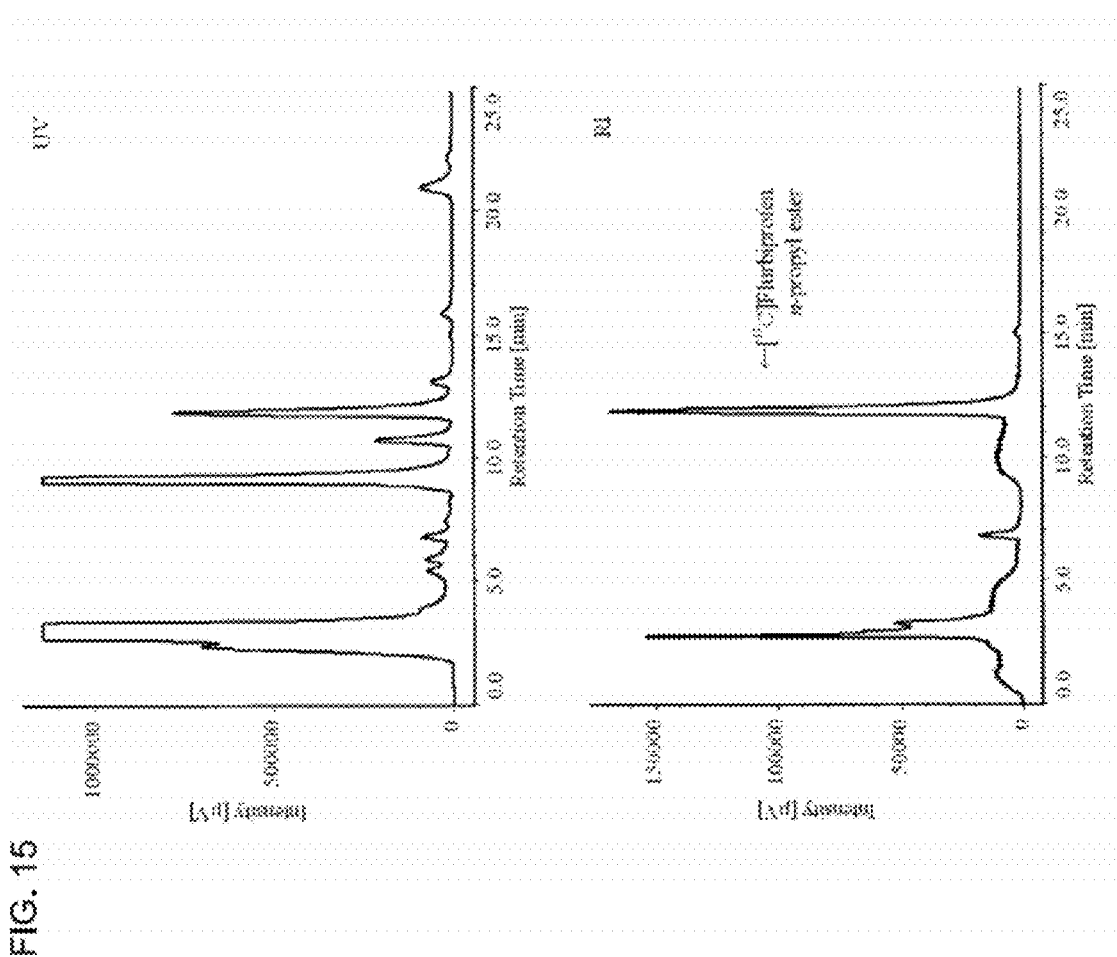
FIG. 15 is a HPLC chart of the reaction mixture in Example 15, and the arrow shows a peak of [¹¹C]flurbiprofen n-propyl ester.
Figure 16:
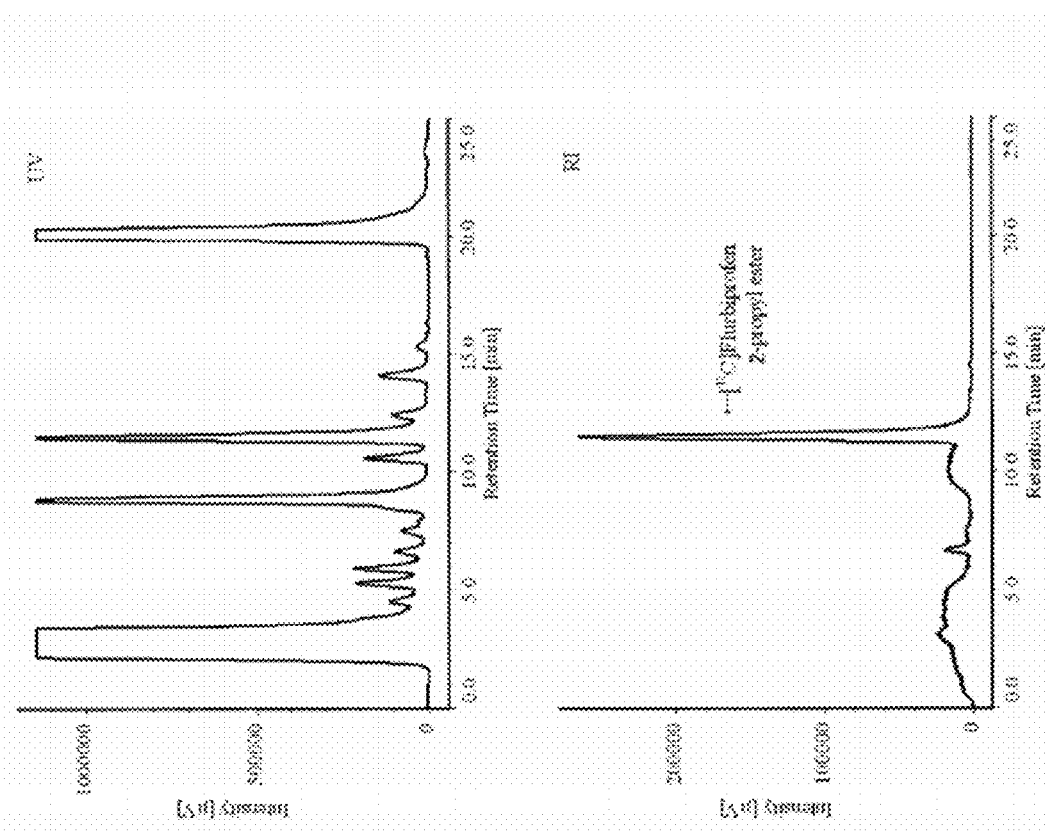
FIG. 16 is a HPLC chart of the reaction mixture in Example 16, and the arrow shows a peak of [¹¹C]flurbiprofen 2-propyl ester.
Figure 17:
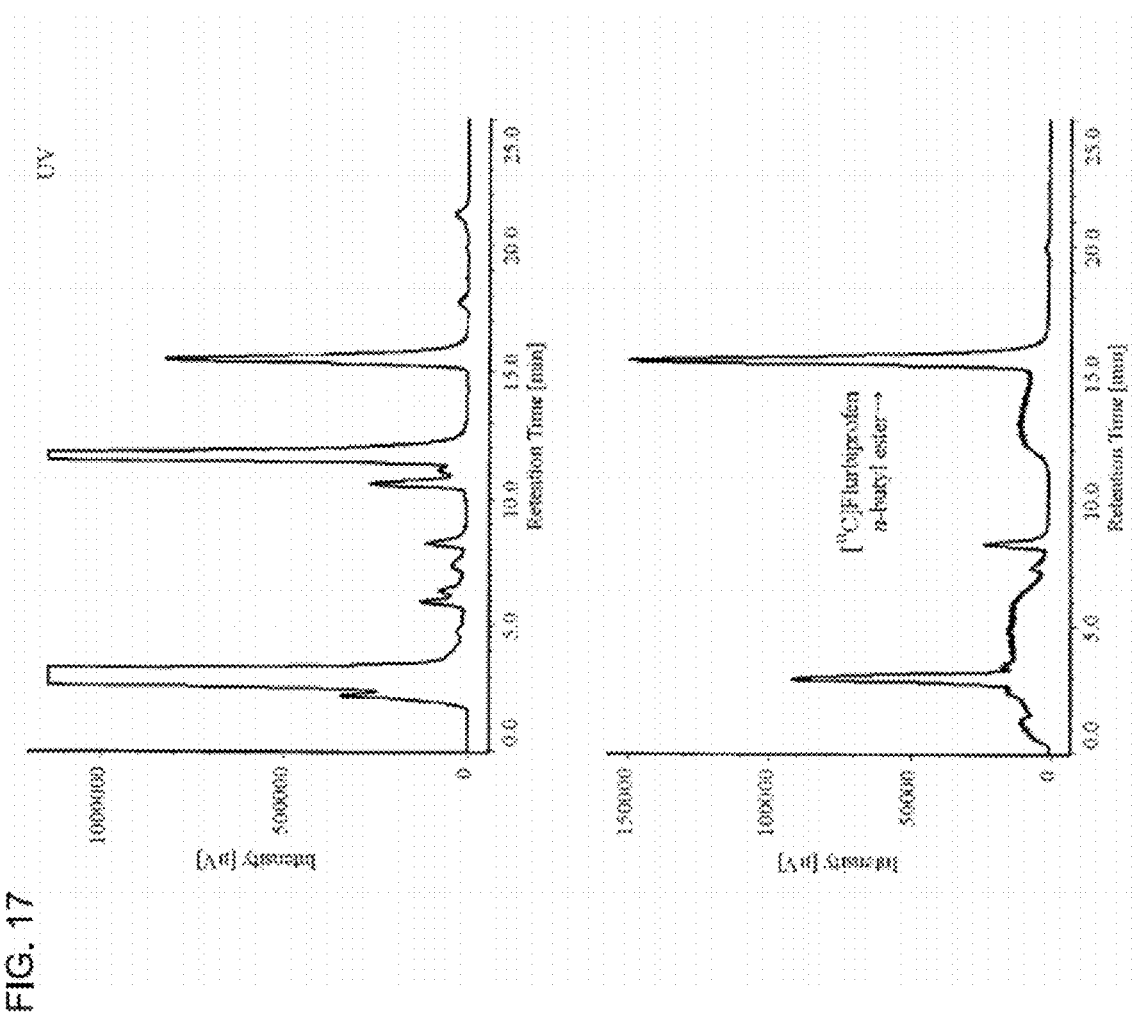
FIG. 17 is a HPLC chart of the reaction mixture in Example 17, and the arrow shows a peak of [¹¹C]flurbiprofen n-butyl ester.
Figure 18:
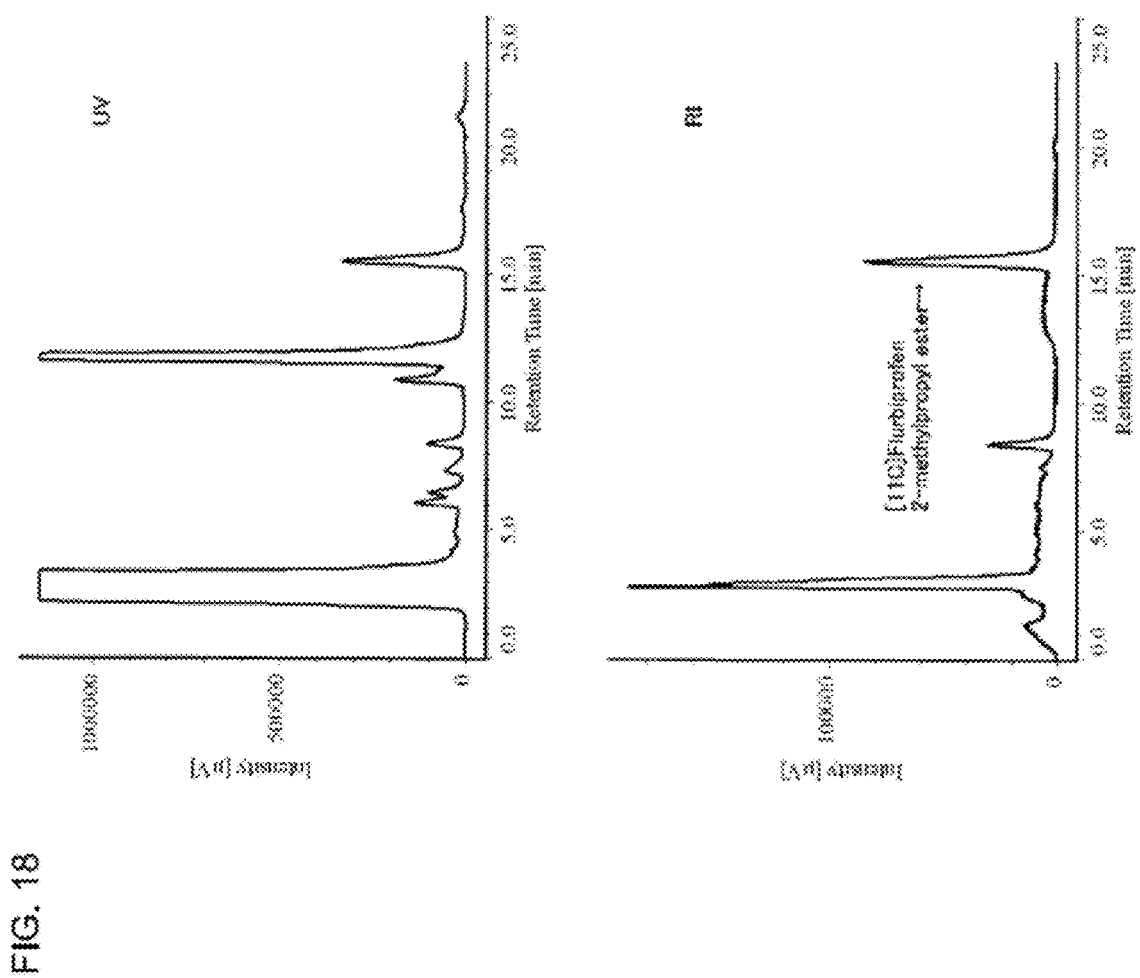
FIG. 18 is a HPLC chart of the reaction mixture in Example 18, and the arrow shows a peak of [¹¹C]flurbiprofen 2-methylpropyl ester.
Figure 19:
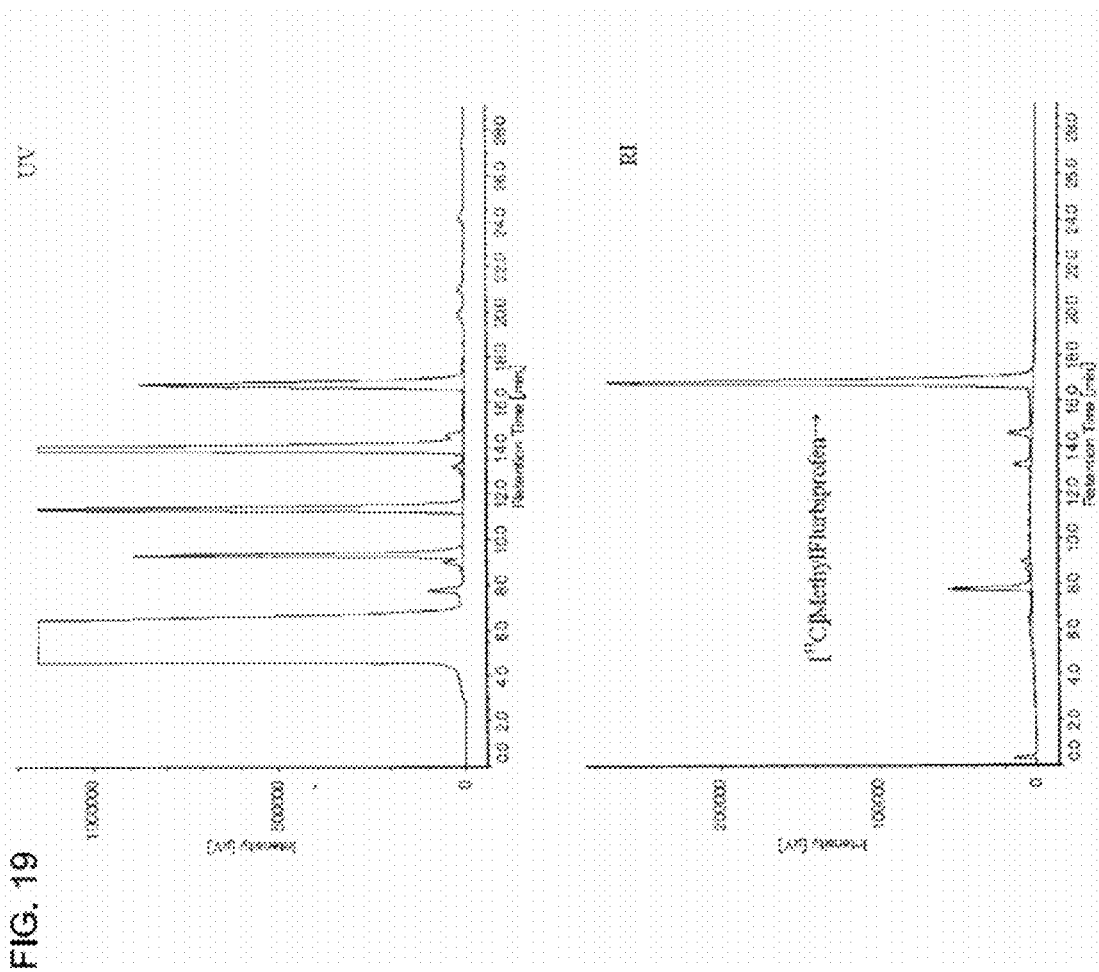
FIG. 19 is a HPLC chart of the reaction mixture in Example 19, and the arrow shows a peak of [¹¹C]methyl flurbiprofen.
Figure 20:
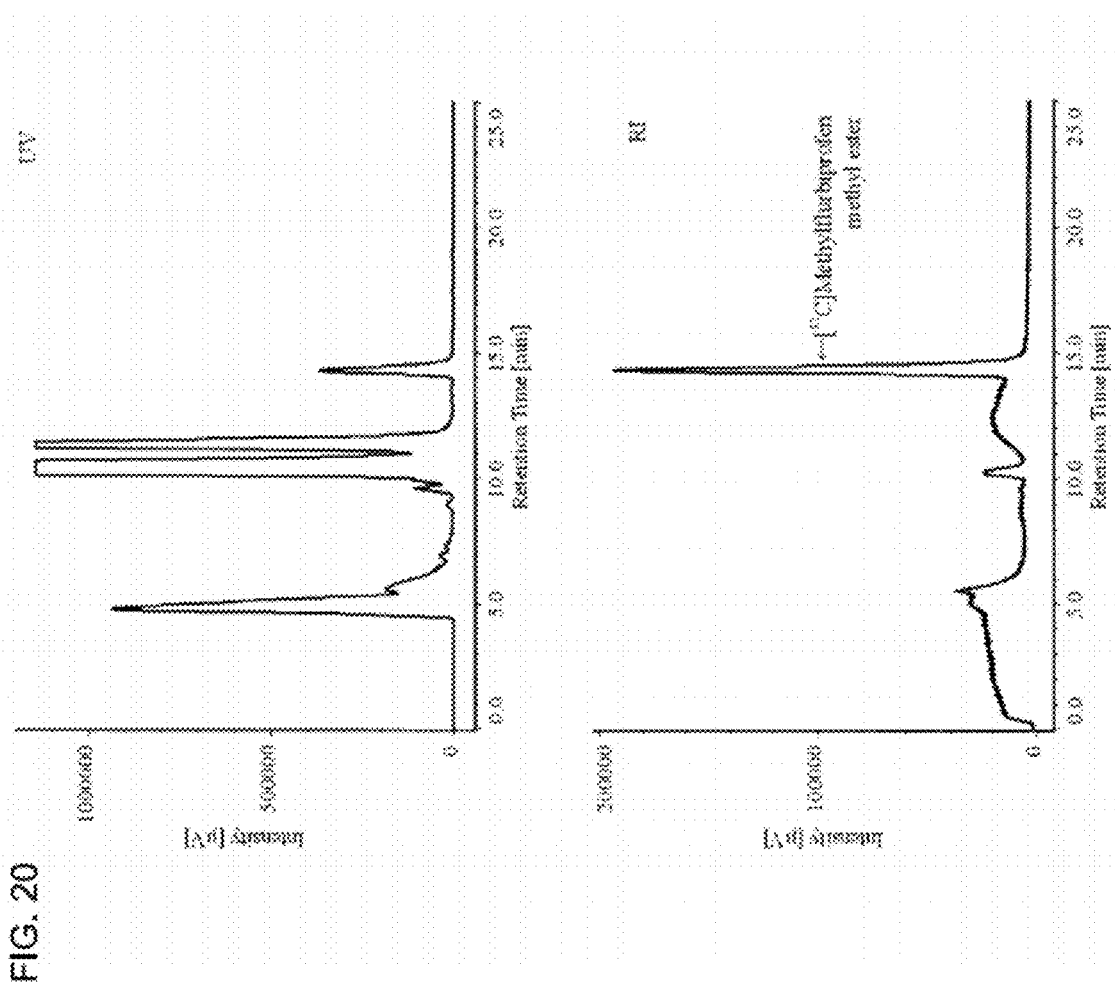
FIG. 20 is a HPLC chart of the reaction mixture in Example 20, and the arrow shows a peak of [¹¹C]methyl flurbiprofen methyl ester.
Figure 21:
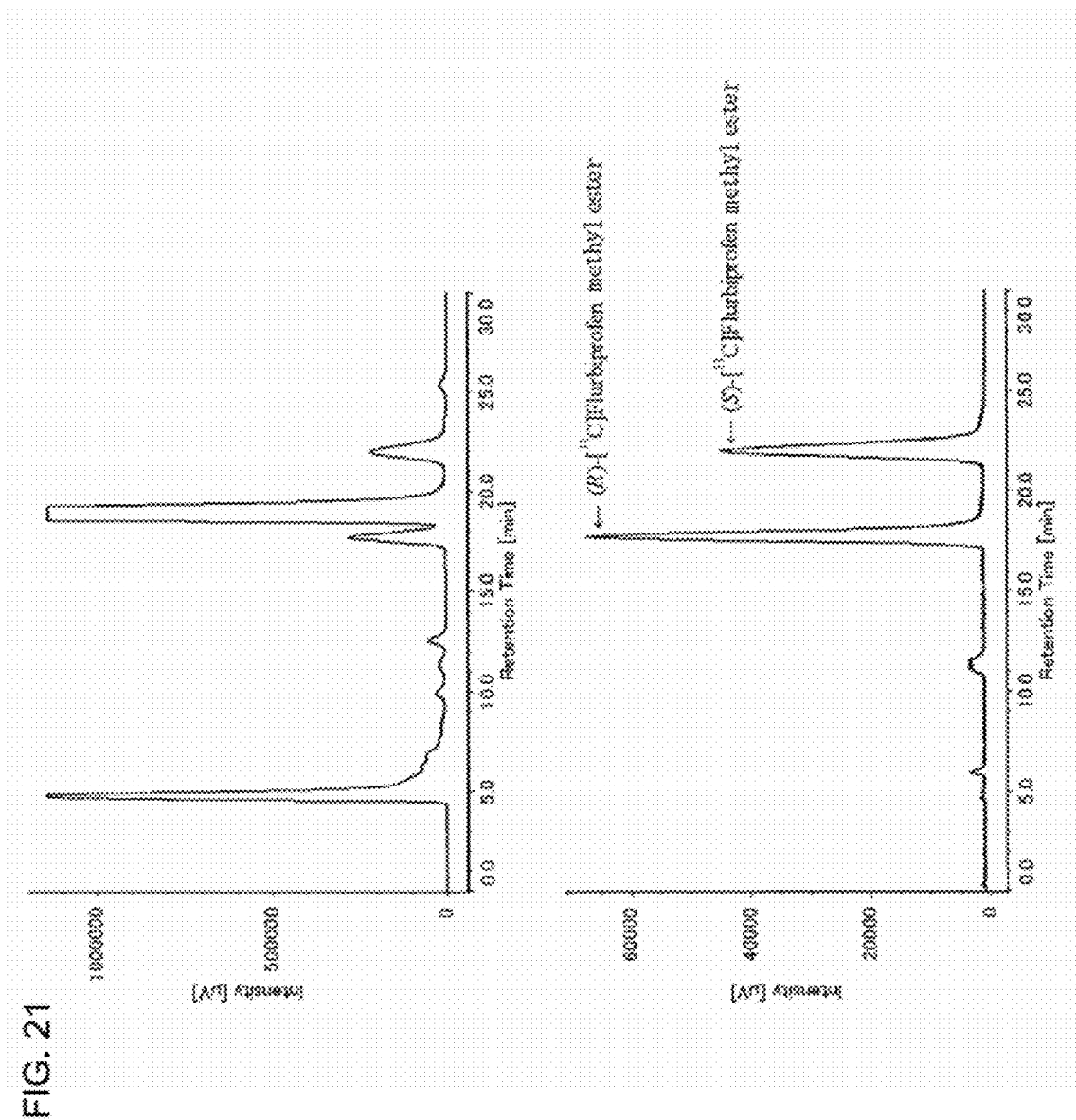
FIG. 21 is a HPLC chart of the reaction mixture in Example 21, and arrows show peaks of (R)—[¹¹C]flurbiprofen methyl ester and (S)—[¹¹C]flurbiprofen methyl ester.
Figure 23:
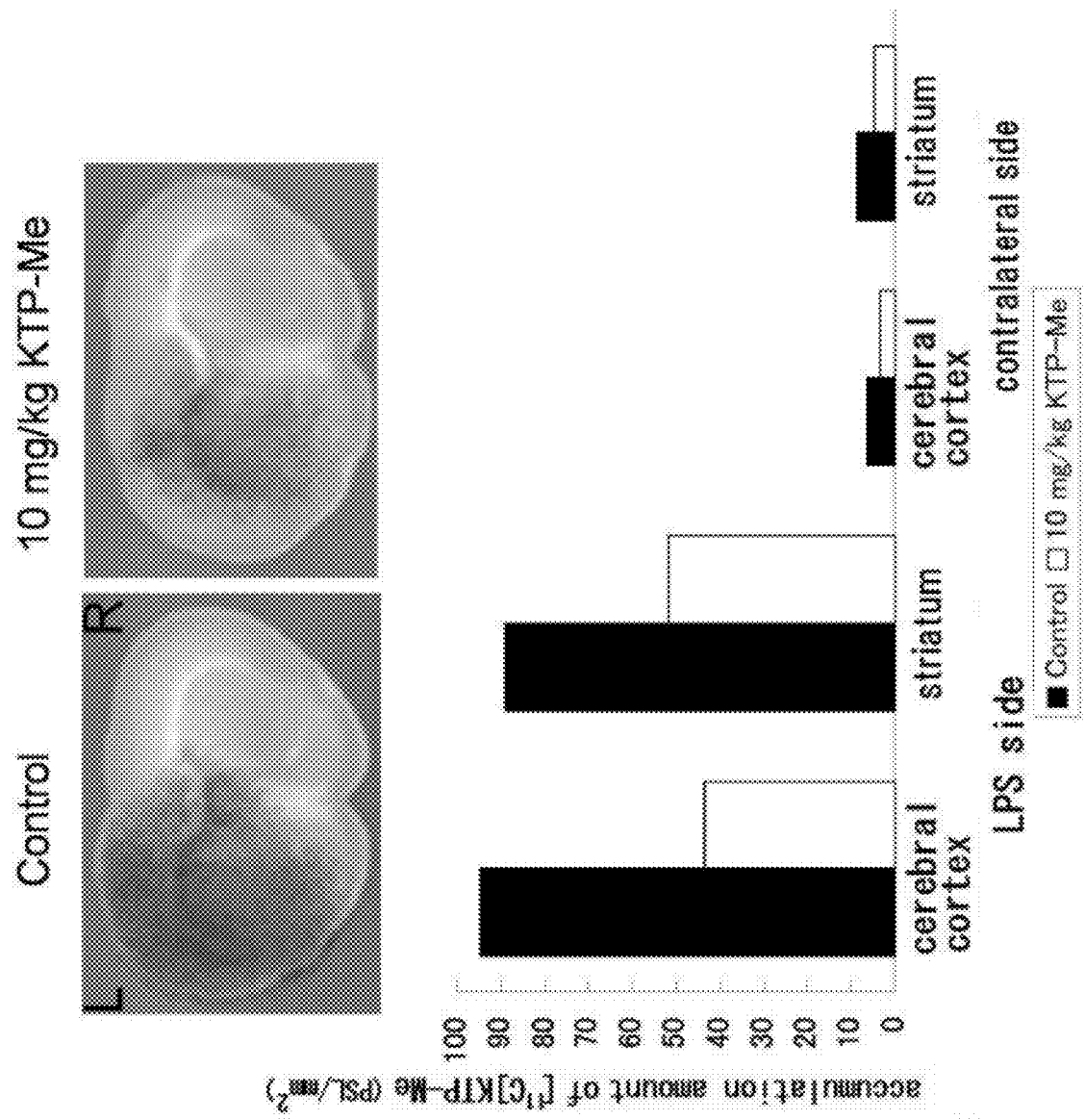
FIG. 23 shows autoradiography of the [¹¹C]ketoprofen methyl ester (described as ¹¹C-KTP-Me) (8) synthesized in Example 6 and a result of its quantitative analysis. In the autoradiography, an image overlapped with a brain section is used, and a quantitative value is shown as $PSL/mm^2$ (photostimulable fluorescence PSL/quantitative area $mm^2$).
Figure 24:
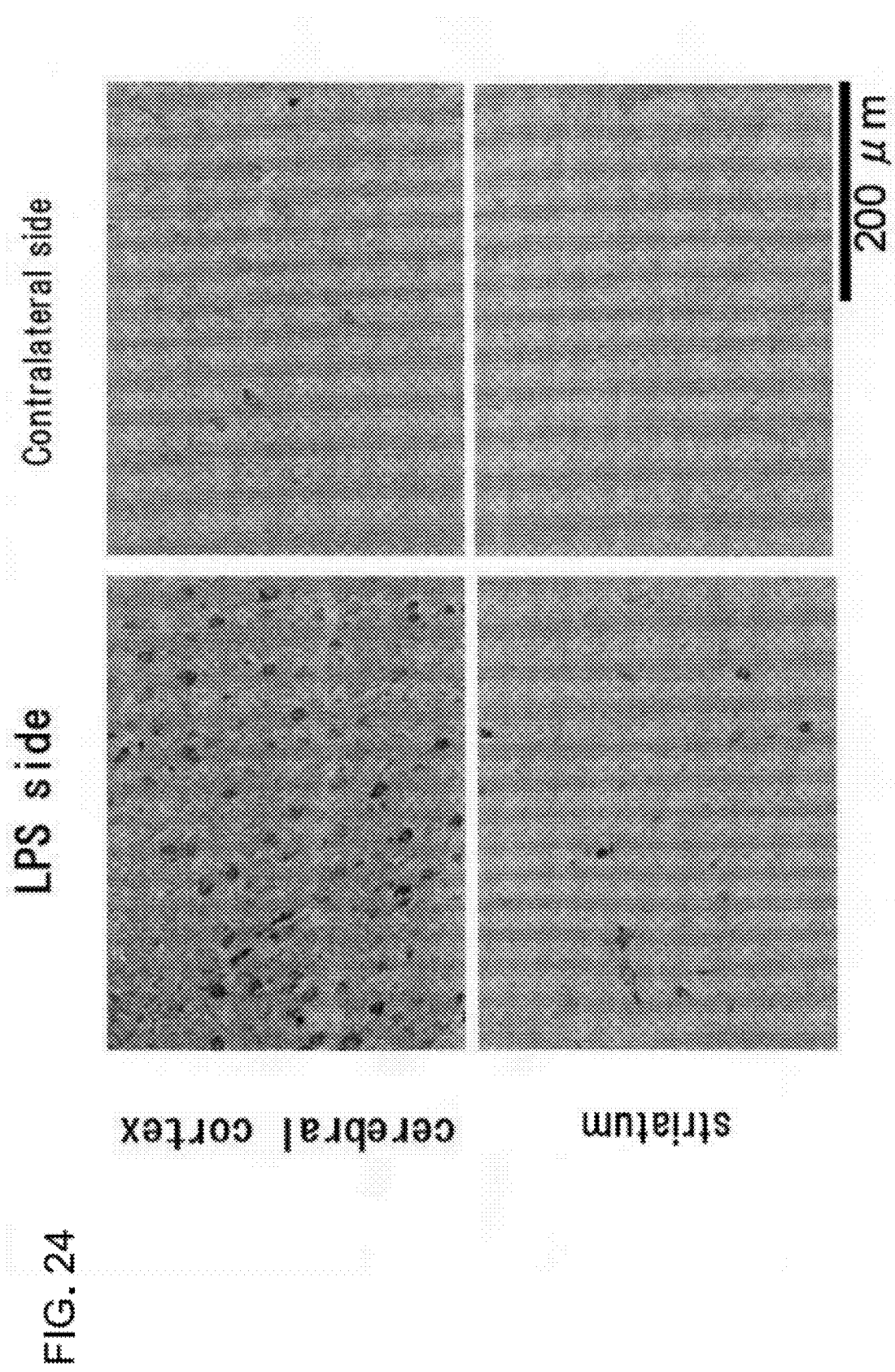
FIG. 24 shows a result of immune tissue chemical staining of cyclooxygenase-2 using a brain section of a rat.
Figure 25:
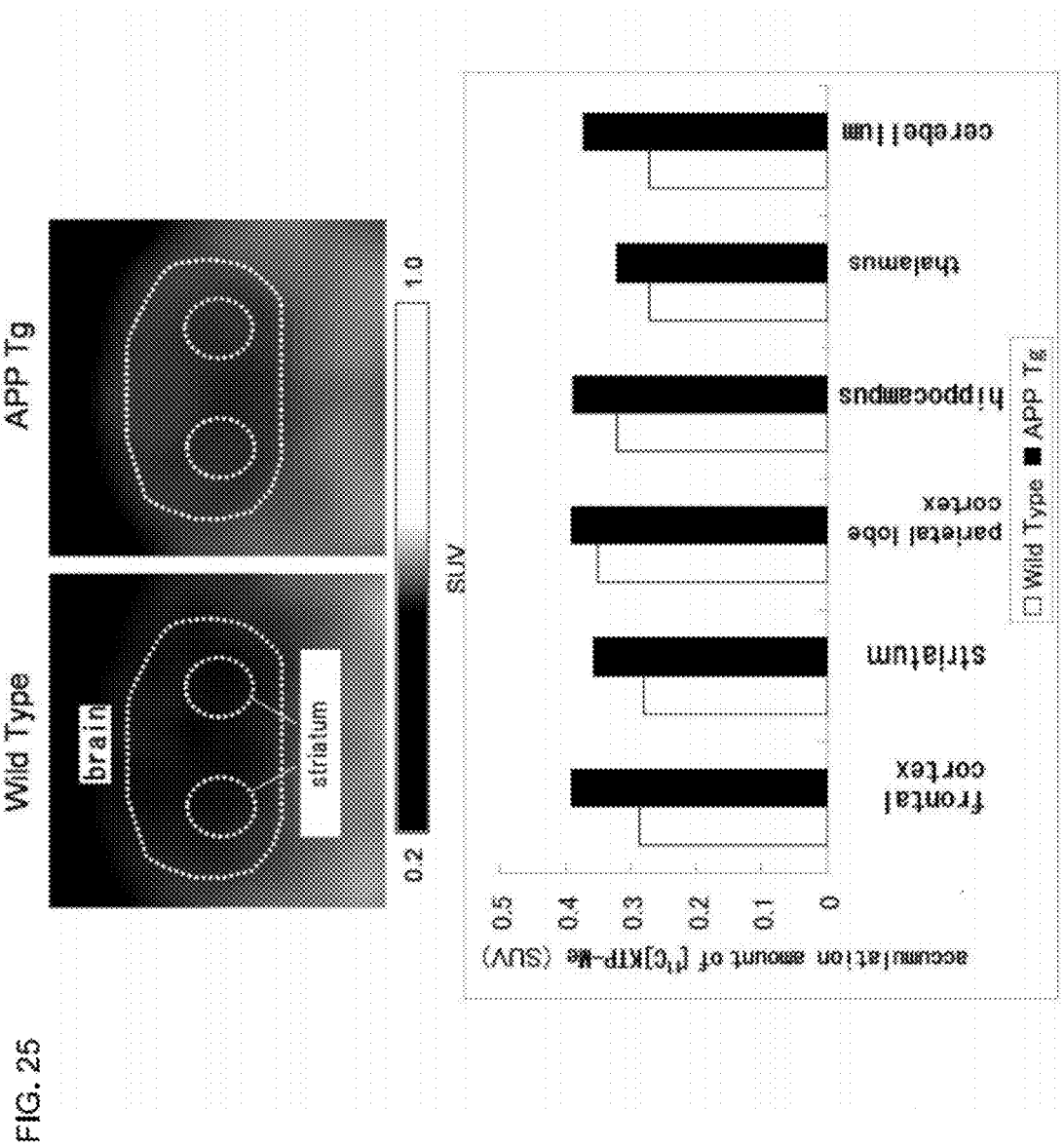
FIG. 25 shows an addition average of PET images for 25 minutes from 5 minutes after administration of the [¹¹C] ketoprofen methyl ester (described as ¹¹C-KTP-Me) (21), and a quantitative value of an accumulation amount into a brain tissue (SUV: tissue radioactivity in region of interest (MBq/g)÷[administration amount (MBq)/body weight (g)]).

The present invention can be used as a molecular probe for PET in the pharmaceutical industry, and the like.

The invention claimed is:

1. An isotope-labeled 2-arylpropionic acid compound represented by chemical formula (1), wherein Ar represents an aryl group which may have a substituent; $R^1$ represents any one of $^{11}CH_3$, $CH_2{}^{18}F$ and $CF_2{}^{18}F$; and $R^2$ represents a hydrogen atom, or an alkyl group which may have a branch, provided that a compound wherein Ar is a benzene ring, $R^1$ is $^{11}CH_3$, and $R^2$ is a hydrogen atom is excluded,
or a pharmaceutically acceptable salt, hydrate, solvate or prodrug thereof

[Chemical Formula 1]

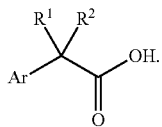

(1)

2. The isotope-labeled 2-arylpropionic acid compound according to claim 1, wherein $R^1$ is $^{11}CH_3$.

3. A process for producing the isotope-labeled 2-arylpropionic acid compounds according to claim 1, comprising
adding a base to a 2-arylacetic acid ester represented by the following chemical formula 2 to generate a carboanion, wherein
Ar represents an aryl group which may have a substituent;
$R^2$ represents a hydrogen atom, or an alkyl group which may have a branch; and
$R^3$ represents a hydrogen atom, an alkyl group which may have a substituent, or an aryl group which may have a substituent, and adding any of $^{11}CH_3X$, $CH_2^{18}FX$ and $CF_2^{18}FX$ to the 2-arylacetic acid to introduce an isotope label, wherein X represents any one of I, Br and a triflate group:

[Chemical Formula 2]

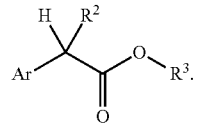

(2)

4. A PET molecular probe comprising the isotope-labeled 2-arylpropionic acid compound according to claim 1 or 2.

5. The PET molecular probe according to claim 4 for PET imaging of cyclooxygenase.

6. The PET molecular probe according to claim 4 for diagnosis of Alzheimer disease.

7. A method of imaging of cyclooxygenase, which comprises:
administering to a body the PET molecular probe according to claim 4, and
imaging the body to generate a PET image.

8. A method of imaging of Alzheimer disease, which comprises:
administering to a body the PET molecular probe according to claim 4, and
imaging the body to generate a PET image.

* * * * *